(12) United States Patent
Jackowski

(10) Patent No.: US 6,780,606 B1
(45) Date of Patent: *Aug. 24, 2004

(54) METHOD FOR DIAGNOSING AND DISTINGUISHING STROKE AND DIAGNOSTIC DEVICES FOR USE THEREIN

(75) Inventor: George Jackowski, Kettleby (CA)

(73) Assignee: SynX Pharma, Inc., Toronto (CA)

(*) Notice: Subject to any disclaimer, the term of this patent is extended or adjusted under 35 U.S.C. 154(b) by 0 days.

This patent is subject to a terminal disclaimer.

(21) Appl. No.: 09/621,592

(22) Filed: Jul. 21, 2000

Related U.S. Application Data

(62) Division of application No. 09/510,700, filed on Feb. 22, 2000.

(30) Foreign Application Priority Data

Feb. 26, 1999 (CA) .............................................. 2263063

(51) Int. Cl.$^7$ ..................... G01N 33/543; G01N 33/566
(52) U.S. Cl. ...................... 435/7.92; 435/7.2; 435/7.21; 436/501; 436/514; 436/518; 436/524; 422/50; 422/60; 422/61; 424/9.1; 424/184.1
(58) Field of Search ............................... 435/7.92, 7.21, 435/7.2, 4, 5, 6, 7, 7.1, 7.4, 7.9, 7.95, 7.94, 970, 973, 975, 792, 13, 969, 9; 436/514, 528, 501, 518, 530, 531, 161, 164, 807, 808, 810, 811, 975; 422/60, 61, 50, 56, 58, 55; 424/9.1, 184.1

(56) References Cited

U.S. PATENT DOCUMENTS

| | | | | |
|---|---|---|---|---|
| 5,290,678 A | * | 3/1994 | Jackowski | ................... 435/7.4 |
| 5,604,105 A | * | 2/1997 | Jackowski | ................... 435/7.4 |
| 5,677,277 A | | 10/1997 | Yatsu et al. | ................... 514/12 |
| 5,710,008 A | * | 1/1998 | Jackowski | ................... 435/7.4 |
| 5,744,358 A | * | 4/1998 | Jackowski | ................... 435/7.4 |
| 5,747,274 A | * | 5/1998 | Jackowski | ................. 435/7.94 |
| 6,235,489 B1 | * | 5/2001 | Jackowski | ................. 435/7.92 |

FOREIGN PATENT DOCUMENTS

WO  WO 98/01471  1/1998  ......... C07K/14/435

OTHER PUBLICATIONS

Sulter et al., "Increased serum neuron specific enolase concentrations in patients with hyperglycemic contcal ischemic stroke.", Neuroscience Letters, vol. 253, 1998, pp. 71–73.*

Strand et al., "Brain and plasma proteins in spinal fluid as markers for brain damage and severity of stroke.", Stroke, 1984, vol. 15, No. 1, pp. 138–144.*

Fassbender et al., "Leakage of brain–originated proteins in peripheral blood: temporal profile and diagnostic value in early ischemic stroke,", Journal of Neurological Sciences, vol. 148, 1997, pp. 101–105.*

Yatsu et al., "Brain Endothelial Cells, Nerve growth Factor: Role in stroke.", Stroke, 1995, vol. 26, No. 1, p. 177.*

Hughet, "Significance of the biologicla assay of NSE (neuron specific enolase). ", Lyon Pharm., 1993, vol. 44, No. 3, pp. 187–192.*

Lamers, K.J.B. et al., Cerebrospinal neuron–specific enolase, S–100 and myelin basic protein in neurological disorders, Acta Neurologica Scandinavica, (1995) 92, pp247–251.

(List continued on next page.)

Primary Examiner—Long V. Le
Assistant Examiner—Lisa V Cook
(74) Attorney, Agent, or Firm—Hamilton, Brook, Smith & Reynolds, P.C.

(57) ABSTRACT

A method for determining whether a subject has had a stroke and, if so, the type of stroke which includes analyzing the subject's body fluid for at least four selected markers of stroke, namely, myelin basic protein, S100 protein, neuronal specific enolase and a brain endothelial membrane protein such as thrombomodulin or a similar molecule. The data obtained from the analyses provide information as to the type of stroke, the onset of occurrence and the extent of brain damage and allow a physician to determine quickly the type of treatment required by the subject.

30 Claims, 10 Drawing Sheets

OTHER PUBLICATIONS

Strand et al., Brain and plasma proteins in spinal fluid as markers for brain damage and severity of stroke, Stroke, (1984) 15, pp138–144.

Garcia–Alix et al., Neuron–specific enolase and myelin basic protein: Relationship of cerebrospinal fluid concentration to the neurologic condition of asphyxiated full–term infants, Pediatrics, (1994) 93 pp234–240.

Cunningham et al., Serum neurone–specific enolase as an indicator of stroke volume, European J. of Clinical Investigation, (1996) 26, pp298–303.

Butterworth et al., Serum neuron–specific enolase, carnosinase and their ratio in acute stroke, Stroke, (1996) 27, 11, pp2064–2068.

Isgro et al., A predictive parameter in patients with brain related complications after cardiac surgery, European J. of Cardio–thoracic Surgery, (1997), 11, pp640–644.

Kaiser et al., Clinical biochemistry of neuron–specific enolase. Clinica Chimica Acta, (1989) 183, pp13–32.

Cunningham et al., Serum neurone–specific enolase (NSE) levels as an indicator of neuronal damage in patients with cerebral infarction, European J. of Clinical Investigation, (1991) 21, pp497–500.

Raabe et al., Fatal secondary increase in serum S–100 protein after severe head injury, J. Neurosurgery, (1999) 91, pp875–877.

Steinberg et al., Experimental brain ischemia: neuron–specific enolase level in cerebrospinal fluid as an index of neuronal damage, J. Neurochem., (1984) 43, 1, pp19–24, Mabe et al., Serum neuron–specific enolase levels after subarachnoid hemorrhage, Surg. Neurol., (1991) 36, pp170–174.

Abraha et al., Serum S–100 protein, relationship to clinical outcome in acute stroke, Ann. Clin. Biochem., (1997) 34, pp546–550.

Rosén et al., Increased serum levels of the S–100 protein are associated with hypoxic brain damage after cardiac arrest, Stroke, (1998), 29, pp473–477.

Kim et al., Serial measurement of interleukin–6, transforming growth factor–β and S–100 protein in patients with acute stroke, Stroke, (1996 27, 9, pp1553–1557.

Westaby et al., Serum S–100 protein: A potential marker for cerebral events during cardiopulmonary bypass, Ann. Thoracic Surgery, (1996) 61, pp88–92.

Büttner et al., S–100 protein: Serum marker of focal brain damage after ischemic territorial MCA infarction, Stroke, (1997) 28, 10, pp1961–1965.

Missler et al., S–100 protein and neuron–specific enolase concentrations in blood as indicators of infarction volume and prognosis in acute ischemic stroke, Stroke, (1997) 28, pp1956–1960.

Wunderlich et al., Early neurobehavorial outcome after stroke is related to release of neurobiochemical markers of brain damage, Stroke, (1999) 30, pp1190–1195.

Wimmer–Greinecker et al., Neuropsychological changes after cardiopulmonary bypass for coronary artery bypass grafting,, Thoracic Cardiovascular Surgery, (1998) 46, pp207–212.

Fassbender et al., Leakage of brain–originated proteins in peripheral blood: temporal profile and diagnostic value in early ischemic stroke, J. of Neurological Sciences, (1997) 148, pp101–105.

Persson et al., S–100 protein and neuron–specific enolase in cerebrospinal fluid and serum: markers of cell damage in human central nervous system, Stroke, (1987) 18, pp911–918.

Härdenmark et al., S–100 protein and neuron–specific enolase in CSF after experimental traumatic or focal ischemic brain damage, J. Neurosurgery, (1989) 71, pp727–731.

Mokuno et al., Neuron–specific enolase and S–100 protein levels in cerebrospinal fluid of patients with various neurological diseases, J. of Neurological Sciences, (1983) 60, pp443–451.

Gao et al., Time–course of neurone–specific enolase and S–100 protein release during and after coronary artery bypass grafting, British J. of Anaesthesia, (1999) 82, 2, pp266–267.

Jansson et al., High concentration of thrombomodulin in plasma is associated with hemorrhage, Circulation, (1997) 96, 9, pp2938–2943.

Aso et al., Mechanisms of elevation of serum and urinary concentrations of soluble thrombomodulin in diabetic patients: Possible application as a marker for vascular endothelial injury, Metabolism, (1998)47, 3, pp362–65.

Kario et al., 'Silent' cerebral infarction is associated with hypercoagulability, endothelial cell damage, and high Lp(a) levels in elderly Japanese, Vascular Biology, (1996) 16, pp734–741.

Fareed et al., Plasma thrombomodulin levels as a predictor of hemorrhage (and thrombotic) events in patients on long–term anticoagulant treatment, Circulation, (1997) 96, pp2765–2768.

Wang et al., Rat brain capillary thrombomodulin structure and function, Thrombosis Research, (1998) 92, pp213–219.

van Dongen et al., Normal serum concentrations of S–100 protein and changes in cerebrospinal fluid concentrations of S–100 protein during and after thoracoabdominal aortic aneuryism surgery: Is S–100 protein a biochemical marker of clinical value in detecting spinal cord ischemia?, J. Vascular Surgery, (1998) 27, 2, pp344–346.

Amiral et al., Design and validation of a new immunoassay for soluble forms of thrombomodulin and studies on plasma, Hybridoma, (1994) 13, 3, pp205–213.

Rothoerl et al., S–100 serum levels after major and minor head injury, The J. of Trauma: Injury, Infection and Critical Care, (1998), 45, 4, pp765–767.

Sulter et al., Increased serum neuron–specific enolase concentrations in patients with hyperglycemic cortical ischemic stroke, Neuroscience Letters, (1998) 29, pp71–73.

Stevens et al., Neurone–specific enolase and N–acetyl–aspartate as potential peripheral markers of ischaemic stroke, European J. of Clinical Investigation, (1999) 29, pp6–11.

van Engelen et al., Age–related changes of neuron–specific enolase, S–100 protein and myelin basic protein concentrations in cerebrospinal fluid, Clin. Chem., (1992) 38, 6, pp813–816.

* cited by examiner

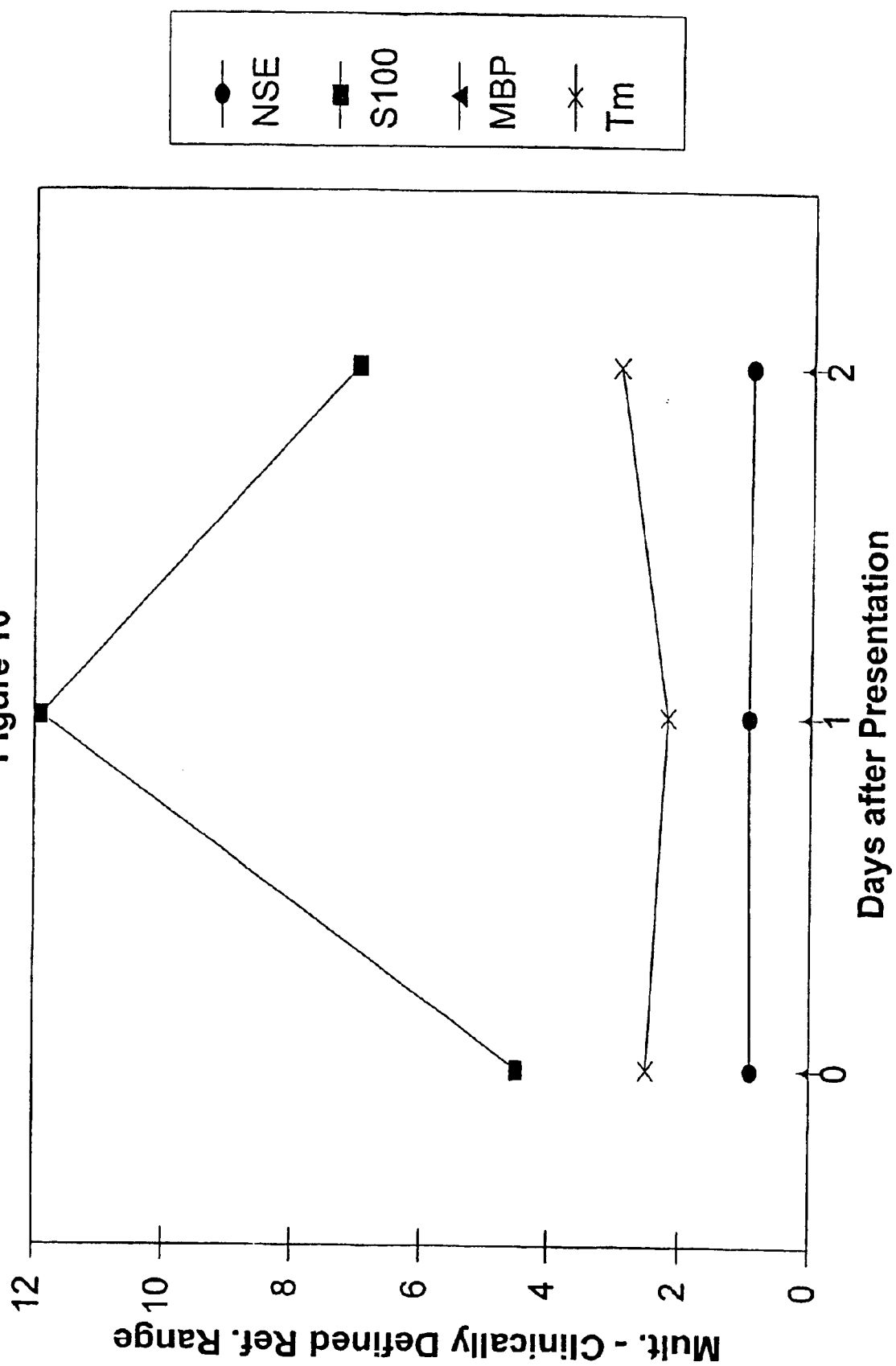

METHOD FOR DIAGNOSING AND DISTINGUISHING STROKE AND DIAGNOSTIC DEVICES FOR USE THEREIN

This is a division of application Ser. No. 09/510,700 filed Feb. 22, 2000.

This application hereby claims foreign priority benefits under 35 USC 119 (a)–(d) of Canadian Patent Application 2,263,063, filed Feb. 26, 1999.

BACKGROUND OF THE INVENTION

This application is directed to a method for diagnosing whether a subject has had a stroke and, if so, differentiating between the different types of stroke. More specifically, the method includes analyzing the subject's body fluid for at least four selected markers of stroke. There are also described diagnostic devices and kits for use in the method.

The impact of stroke on the health of human beings is very great when considered in terms of mortality and even more devastating when disability is considered. For example, stroke is the third leading cause of death in adults in the United States, after ischemic heart disease and all forms of cancer. For people who survive, stroke is the leading cause of disability. The direct medical costs due to stroke and the cost of lost employment amount to billions of dollars annually. Approximately 85% of all strokes are ischemic (thrombotic and embolic) with the remainder being hemorrhagic.

Stroke is an underserved market for both therapeutics and diagnostic techniques. In the United States alone over 700,000 people have strokes each year. A multiple of that number would be suspected of having strokes with diagnostics only confirmed by expensive technology including computer-assisted tomography (CAT) scans and magnetic resonance imaging (MRI). However, these sophisticated technologies are not available in all hospitals and they are also not sensitive enough to diagnose ischemic stroke at an early stage.

Stroke is a clinical diagnosis made by a neurologist, usually as a consultation. Current methods for diagnosing stroke include symptom evaluation, medical history, chest X-ray, ECG (electrical heart activity), EEG (brain nerve cell activity), CAT scan to assess brain damage and MRI to obtain internal body visuals. A number of blood tests may be performed to search for internal bleeding. These include complete blood count, prothrombin time, partial thromboplastin time, serum electrolytes and blood glucose.

Determining the immediate cause of a stroke can be difficult especially upon presentation where the diagnosis relies mainly on imaging techniques. Approximately 50% of cerebral infarctions are not visible on a CAT scan. Further, even though a CAT scan can be very sensitive for the identification of hemorrhagic stroke, it is not very sensitive for cerebral ischemic during evaluation of stroke and is usually positive at from 24 to 36 hours after onset of stroke. As a result a window of opportunity for rapid treatment would usually have expired once the current diagnostic techniques positively identify a stroke.

The treatment of stroke includes preventive therapies such as antihypertensive and antiplatelet drugs which control and reduce blood pressure and thus reduce the likelihood of stroke. Also, the development of thrombolytic drugs such as t-PA (tissue plasminogen activator) has provided a significant advance in the treatment of ischemic stroke victims but to be effective and minimize damage from acute stroke it is necessary to begin treatment very early, for example, within about three hours after the onset of symptoms. These drugs dissolve blood vessel clots which block blood flow to the brain and which are the cause of approximately 80% of strokes. However, these drugs can also present the side effect of increased risk of bleeding. Various neuroprotectors such as calcium channel antagonist can stop damage to the brain as a result of ischemic insult. The window of treatment for these drugs is typically broader than that for the clot dissolvers and they do not increase the risk of bleeding.

Diagnostic techniques for the early diagnosis of stroke and identification of the type of stroke are needed to allow the physician to prescribe the appropriate therapeutic drugs at an early stage in the cerebral event. Various markers for stroke are known and analytical techniques for the determination of such markers have been described in the art. As used herein the term "marker" refers to a protein or other molecule that is released from the brain during a cerebral ischemic or hemorrhagic event. Such markers include isoforms of proteins that are unique to the brain.

It has been reported in the literature that myelin basic protein (MBP) concentration, in cerebrospinal fluid (CSF) increases after sufficient damage to neuronal tissue, head trauma and AIDS dementia. Further, it has been reported that ultrastructural immunocytochemistry studies using anti-MBP antibodies have shown that MBP is localized exclusively in the myelin sheath. Thus, it has been suggested that MBP levels in CSF or serum be used as a marker of cerebral damage in acute cerebrovascular disease. See Strand, T., et al., Brain and plasma proteins in spinal fluid as markers for brain damage and severity of stroke, Stroke (1984) 15; 138–144. The increase in MBP concentration in CSF is most evident in about four to five days after the onset of thrombotic stroke while in cerebral hemorrhage the increase was highest almost immediately after onset. See Garcia-Alex, A., et al., Neuron-specific enolase and myelin basic protein: Relationship of cerebrospinal fluid concentration to the neurologic condition of asphyxiated fill-term infants, Pediatrics (1994) 93; 234–240. It has also been found that patients with transitory ischemic attack (TIA) had normal CSF values for MBP while those with cerebral infarction and hemorrhage had elevated values. In cerebral infarction there was a significant increase in MBP concentration in CSF from the first to second lumbar puncture while patients with intracerebral hemorrhage had reached already markedly elevated levels at the first lumbar puncture. It was reported that the kinetic difference in MBP release may be useful in the differential diagnosis of hemorrhagic and ischemic stroke. MBP levels a in CSF also correlated to the visibility of the cerebral lesion at CT scan and to the short-term outcome of the patients. Further, the concentration of MBP increased with the extent of brain lesion and high values indicated a poor short-term prognosis for the patient. See Strand, T. et al, previously cited.

S100 protein is another marker which may be taken as a useful marker for assessing neurologic damage and for determining the extent of brain damage and for determining the extent of brain lesions. Thus, it has been suggested for use as an aid in the diagnosis and assessment of brain lesions and neurological damage due to stroke. See Missler, U., Weismann, M., Friedrich, C. and Kaps, M., S100 protein and neuron-specific enolase concentrations in blood as indicators of infarction volume and prognosis in acute ischemic stroke, Stroke (1997) 28; 1956–60.

Neuron-specific enolase (NSE) also has been suggested as a useful marker of neurologic damage in the study of stroke with particular application in the assessment of treatment. See Teasdale, G. and Jennett, B., Assessment of coma and impaired consciousness, Lancet (1974) 2; 81–84.

There continues to be a need for diagnostic techniques which can provide timely information concerning the type of stroke suffered by a patient, the onset of occurrence, the location of the event, the identification of appropriate patients who will benefit from treatment with the appropriate drug and the identification of patients who are at risk of bleeding as a result of treatment. Such techniques can provide data which will allow a physician to determine quickly the appropriate treatment required by the patient and permit early intervention.

It is therefore an object of this invention to provide a method for rapidly diagnosing and distinguishing stroke.

It is a further object of the invention to provide a method for distinguishing between thrombotic strokes and hemorrhagic strokes.

It is another object of the invention to provide such a method which includes analyzing the body fluid of a patient for at least four markers of stroke.

It is yet another object to provide a method which can provide information relating to the time of onset of the stroke.

It is still another object to provide diagnostic assay devices for use in the method.

SUMMARY OF THE INVENTION

These and other objects and advantages are accomplished in accordance with the invention by providing a method that is capable of determining whether a patient has suffered a stroke and, if so, whether the event is thrombotic or hemorrhagic. According to the method, a body fluid of the patient is analyzed for four molecules which are cell type specific, three of which are specific ischemic markers, namely S100 protein, myelin basic protein (MBP) and specific neuronal enolase (NSE) and one brain endothelial membrane protein, for example, thrombomodulin (Tm). The method analyzes the isoforms of the marker proteins which are specific to the brain.

The analyses of these markers may be carried out on the same sample of body fluid or on multiple samples of body fluid. In the latter embodiment the different body fluid samples may be taken at the same time or at different time periods.

The information which is obtained according to the method of the invention can be provided at the critically important early stages of a stroke, e.g., within the first three to six hours after onset of symptoms since the analysis of the patient's body fluid can be carried out in about 45 to 50 minutes after the body fluid is collected. The data can be vital to the physician by assisting in the determination of how to treat a patient presenting with symptoms of stroke or suspected of having a stroke. The data can rule stroke in or out, and differentiate between ischemic and hemorrhagic stroke and therefore exclude hemorrhagic stroke patients from being given clot dissolving therapeutics because of the risk of increased bleeding. The data can also identify patients who are at risk of bleeding as a result of treatment, i.e., patients with compromised brain vasculature. Further, the method can provide at an early stage is prognostic information relating to the outcome of intervention which can improve patient selection for appropriate therapeutics and intervention. The method of the invention is diagnostic well before the imaging technologies. In addition, these data can indicate the location of the stroke within the brain and the extent of damage to the brain as well as determine whether the extent of the stroke is increasing. The cerebral infarct associated with stroke, made up of dead and dying brain tissue, which forms because of inadequate oxygenation typically increases in size during the acute period after ischemic begins. By measuring the markers in samples of body fluid taken at different points in time the progress of the stroke can be ascertained.

BRIEF DESCRIPTION OF THE DRAWINGS

The invention will now be described further in detail with respect to various preferred embodiments thereof in conjunction with the accompanying drawings wherein:

FIG. 10 illustrates that patient SJ-1 had a cerebral infarct and because of the elevated Tm level was at risk of hemorrhage if given thrombolytics because of the endothelial vasculature being compromised.

DESCRIPTION OF THE PREFERRED EMBODIMENTS

Figure 1:
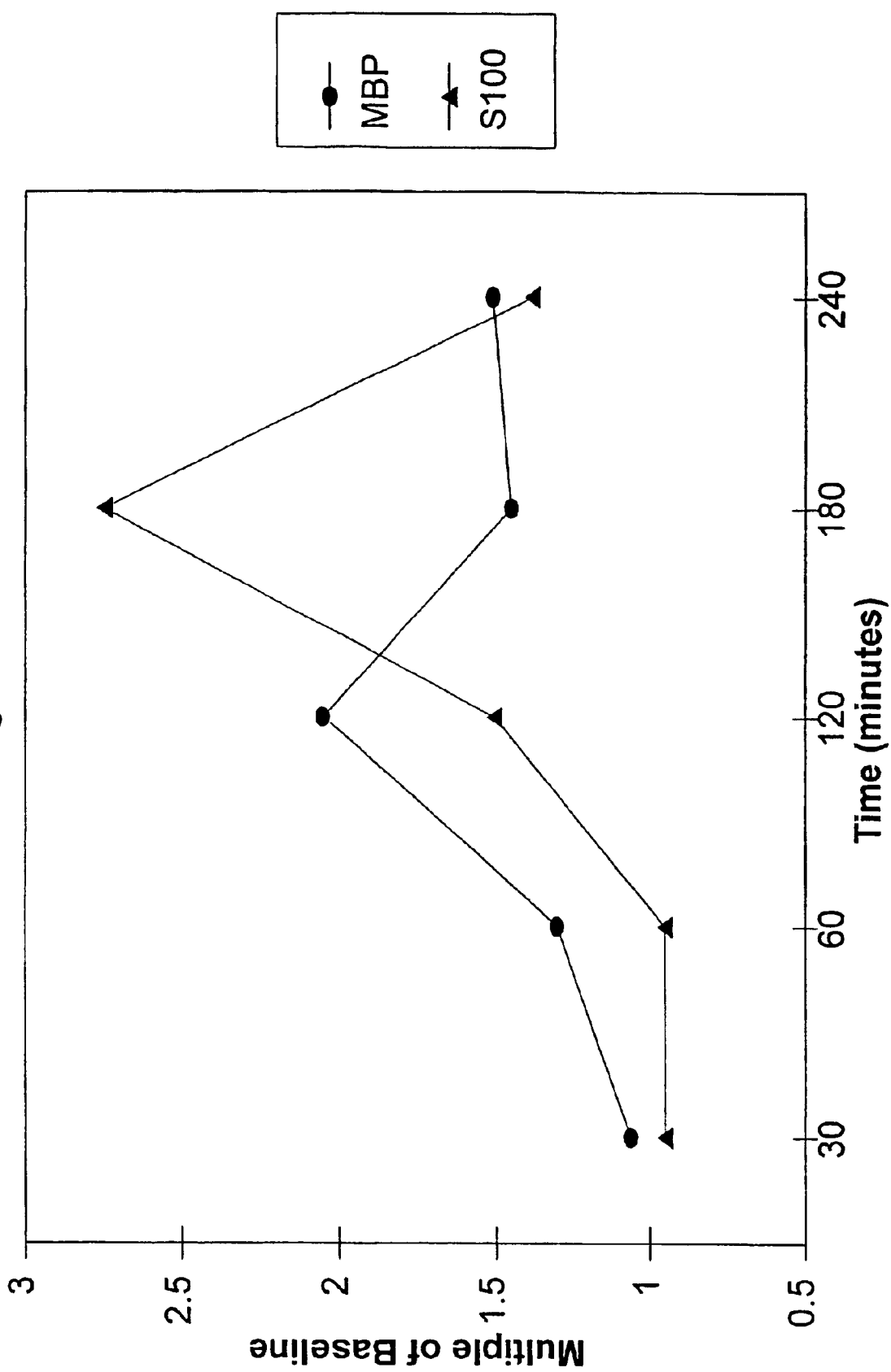
FIG. 1 is a graphical illustration of the concentration over time (in minutes) of two marker proteins which are indicative of cerebral condition or status.

The markers which are analyzed according to the method of the invention are released into the circulation and are present in the blood and other body fluids. Preferably blood, or any blood product that contains them such as, for example, plasma, serum, cytolyzed blood (e.g., by treatment with hypotonic buffer or detergents), and dilutions and preparations thereof is analyzed according to the invention. In another preferred embodiment the concentration of the markers in CSF is measured.

The terms "above normal" and "above threshold" are used herein to refer to a level of a marker that is greater than the level of the marker observed in normal individuals, that is, individuals who are not undergoing a cerebral event, i.e. an injury to the brain which may be ischemic, mechanical or infectious. For some markers, no or infinitesimally low levels of the marker may be present normally in an individual's blood. For others of the markers analyzed for according to the invention, detectable levels may be present normally in blood Thus, these terms contemplate a level that is significantly above the normal level found in individuals. The term "significantly" refers to statistical significance and generally means a two standard deviation (SD) above normal, or higher, concentration of the marker is present. The assay method by which the analysis for any particular marker protein is carried out must be sufficiently sensitive to be able to detect the level of the marker which is present over the concentration range of interest and also must be highly specific.

The four primary markers which are measured according to the present method are proteins which are released by the specific brain cells as the cells become damaged during a cerebral event. These proteins can be either in their native form or immunologically detectable fragments of the proteins resulting, for example, by enzyme activity from proteolytic breakdown. The specific four primary markers when mentioned in the present application, including the claims hereof, are intended to include fragments of the proteins which can be immunologically detected. By "immunologically detectable" is meant that the protein fragments contain an epitope which is specifically recognized by a cognate antibody.

As mentioned previously, the markers analyzed according to the method of the invention are cell type specific. Myelin basic protein (MBP) is a highly basic protein, localized in the myelin sheath, and accounts for about 30% of the total protein of the myelin in the human brain. The protein exists as a single polypeptide chain of 170 amino acid residues which has a rod-like structure with dimensions of 1.5×150 nm and a molecular weight of about 18,500 Dalton. It is a flexible protein which exists in a random coil devoid of $\alpha$ helices $\beta$ conformations.

The increase of MBP concentration in blood and CSF is most evident about four to five days after the onset of ischemic stroke while in cerebral hemorrhage the increase is highest almost immediately after the onset. Further, patients with TIA have normal values for MBP while those with cerebral infarction and intercerebral hemorrhage have elevated values. A normal value for a person who has not had a cerebral event is from 0.00 to about 0.016 ng/mL. MBP has a half-life in serum of about one hour and is a sensitive marker for cerebral hemorrhage.

The S100 protein is a cytoplasmic acidic calcium binding protein found predominantly in the gray matter of the brain, primarily in glia and Schwann cells. The protein exists in several homo- or heterodimeric isoforms consisting of two immunologically distinct subunits, alpha (MW=10,400 Dalton) and beta (MW=10,500 Dalton) while the S100a$\sigma$ is the homodimer act which is found mainly in striated muscle, heart and kidney. The S100b isoforms is the 21,000 Dalton homodimer $\beta\beta$. It is present in high concentration in glia cells and Schwann cells and is thus tissue specific. It is released during acute damage to the central nervous system and is a sensitive marker for cerebral infarction. According to the method of the invention, the assay is specific for the $\beta$-subunit of the S100 protein.

The S100b isoform is a specific brain marker released during acute damage to the central nervous system. It is eliminated by the kidney and has a half-life of about two hours in human serum. Repeated measurements of S100 serum levels are useful to follow the course of neurologic damage. Additionally, the presence of elevated S100 levels in CSF or serum, in association with stroke symptoms, can be useful in the differential diagnosis of stroke and may be a valuable indicator of cerebral infarction.

The enzyme enolase (EC 4.2.1.11) catalyzes the interconversion of 2-phosphoglycerate and phosphoenolpyruvate in the glycolytic pathway. The enzyme exists in three isoproteins each the product of a separate gene. The gene loci have been designated ENO1, ENO2 and ENO3. The gene product of ENO1 is the nonneuronal enolase (NNE or $\alpha$), which is widely distributed in various mammalian tissues. The gene product of ENO2 is the muscle specific enolase (MSE or $\beta$) which is localized mainly in the cardiac and striated muscle, while the product of the ENO3 gene is the neuronal specific enolase (NSE or $\gamma$) which is largely found in the neurons and neuroendocrine cells. The native enzymes are found as homo- or heterodimeric isoforms composed of three immunologically distinct subunits, $\alpha$, $\beta$ and $\gamma$. Each subunit has a molecular weight of approximately 39,000 Dalton.

The $\alpha\gamma$ and $\gamma\gamma$ enolase isoforms, which have been designated neuronal specific enolase (NSE) each have a molecular weight of approximately 80,000 Dalton. It has been shown that NSE concentration in CSF increases after experimental focal ischemic and the release of NSE from damaged cerebral tissue into the CSF reflects the development and size of the infarcts. NSE has a serum half-life of about 48 hours and its peak concentration has been shown to occur later after cerebral artery (MCA) occlusion. NSE levels in CSF have been found to be elevated in acute and/or extensive disorders including subarachnoid hemorrhage and acute cerebral infarction.

The fourth marker protein measured according to the invention is a brain endothelial membrane protein. Endothelial cells which line the small blood vessels of the brain possess a unique expression of cell surface, receptors, transporters and intracellular enzymes that serve to tightly regulate exchange of solutes between blood and brain parenchyma. Brain endothelial membrane proteins include: Thrombomodulin (Tm), a 105,000 Dalton surface glycoprotein involved in the regulation of intravascular coagulation; Glucose Transporter (Gluc 1), a 55,000 Dalton cell surface transmembrane protein which may exist in dimeric or tetrameric form; Neurothelin/HT7, a 43,000 Dalton protein integrated into the cytoplasmic membrane transport protein; Gamma Glutamyl Transpeptidase, a protein which is found as a heterodimeric isoform composed of 22,000 and 25,000 Dalton subunits and is involved in the transfer of gamma glutamyl residue from glutathione to amino acids; and P-glycoprotein, a multidrug resistant membrane spanning protein. In a preferred embodiment of the method Tm is the brain endothelial membrane protein which is measured. Tm is a sensitive marker for lacunar infarcts.

The data obtained according to the method indicate whether a stroke has occurred and, if so, the type of stroke, the localization of the damage and the spread of the damage. Where the levels of all four markers are negative, i.e., within the normal range, there is no cerebral injury. When only the brain endothelial membrane protein, e.g., Tm, is elevated, or positive, i.e., the level is at least 2SD above normal, the stroke is a lacunar infarct present in the basal ganglia and deep white matter of the brain. When the NSE level is positive and the S100 and/or MBP levels are negative (the brain endothelial membrane protein marker is positive or negative) the patient has suffered a TIA.

According to another preferred embodiment, a fifth marker, which is from the specific cell type of one of the three ischemic markers analyzed according to the method of the invention, is measured to provide information related to the time of onset of the stroke. It should be recognized that the onset of stroke symptoms is not always known, particularly if the patient is unconscious or elderly and a reliable clinical history is not always available. An indication of the time of onset of the stroke can be obtained by relying on the differing release kinetics of brain markers having different molecular weights. The time release of brain markers into the circulation following brain injury is dependent on the size of the marker, with smaller markers tending to be released earlier in the event while larger markers tend to be released later. FIG. 1 illustrates the release kinetics of two marker proteins which are analyzed according to the method of the invention, namely MBP and S100. These data were obtained from fluid collected from the brain tissue of a pig after coronary bypass surgery was performed. The samples were collected at 0, 30, 120, 180 and 240 minutes after the subject had been removed from the bypass machine. The concentration values are expressed in multiples of a baseline value which was the concentration at time zero. These data indicate that the release of MBP (MW=18,500) appears to reach a maximum about 120 minutes after the ischemic event whereas the release of S100 (MW=21,000) does so at after about 180 minutes. Thus, by measuring an additional protein marker from the specific cell type of one of the three ischemic markers utilized in the method of the invention, data relating to the time of onset can be obtained. The time of onset is defined as the moment of onset of clinical symptoms of stroke. In this preferred embodiment the second marker protein is a larger, i.e., a higher molecular weight marker, than the primary marker of the same cell type.

The three ischemic markers utilized according to the invention and various other high molecular weight markers from the same specific cell type are shown in Table I.

TABLE I

| MARKER | SIZE (D) | SMALLEST FRAGMENT (D) |
|---|---|---|
| SPECIFIC GLIAL MARKERS: | | |
| S100 | 21,000 | 10,500 |
| Growth Associated Protein 43 (GAP-43) | 43,000 | 43,000 |
| Glutamine Synthetase (GS) | 400,000 | 44,000 |
| Glial Fibrillary Acid Protein (GFAP) | 51,000 | 51,000 |
| Glycine Transporter (GLYT1) | 50–70,000 | 50–70,000 |
| Glycine Transporter (GLYT2) | 90–110,000 | 90–110,000 |
| SPECIFIC NEURONAL MARKERS: | | |
| Neuron Specific Enolase (NSE) | 78,000 | 39,000 |
| Neruon Specific Glycoprotein (GP50) | 42,000 | 42,000 |
| Calpain | 80,000 | 55,000 |
| Neurofibrillary Protein (NF) | 68,000 | 68,000 |
| Heat Shock Protein 72 (HSP-72) | 72,000 | 72,000 |
| Beta Amyloid Precursor Protein (beta APP) | 250,000 | 125,000 |
| SPECIFIC AXONAL MARKERS: | | |
| Myelin Basic Protein (MBP) | 18,500 | 18,500 |
| Calbindin D-28K | 28,000 | 28,000 |
| Proteolipid Protein (PLP) | 23–30,000 | 23–30,000 |
| Myelin Associated Glycoprotein (MAG) | 90–100,000 | 58,000 |
| Neurofilament H (HFN) | 200,000 | 200,000 |

Figure 2:
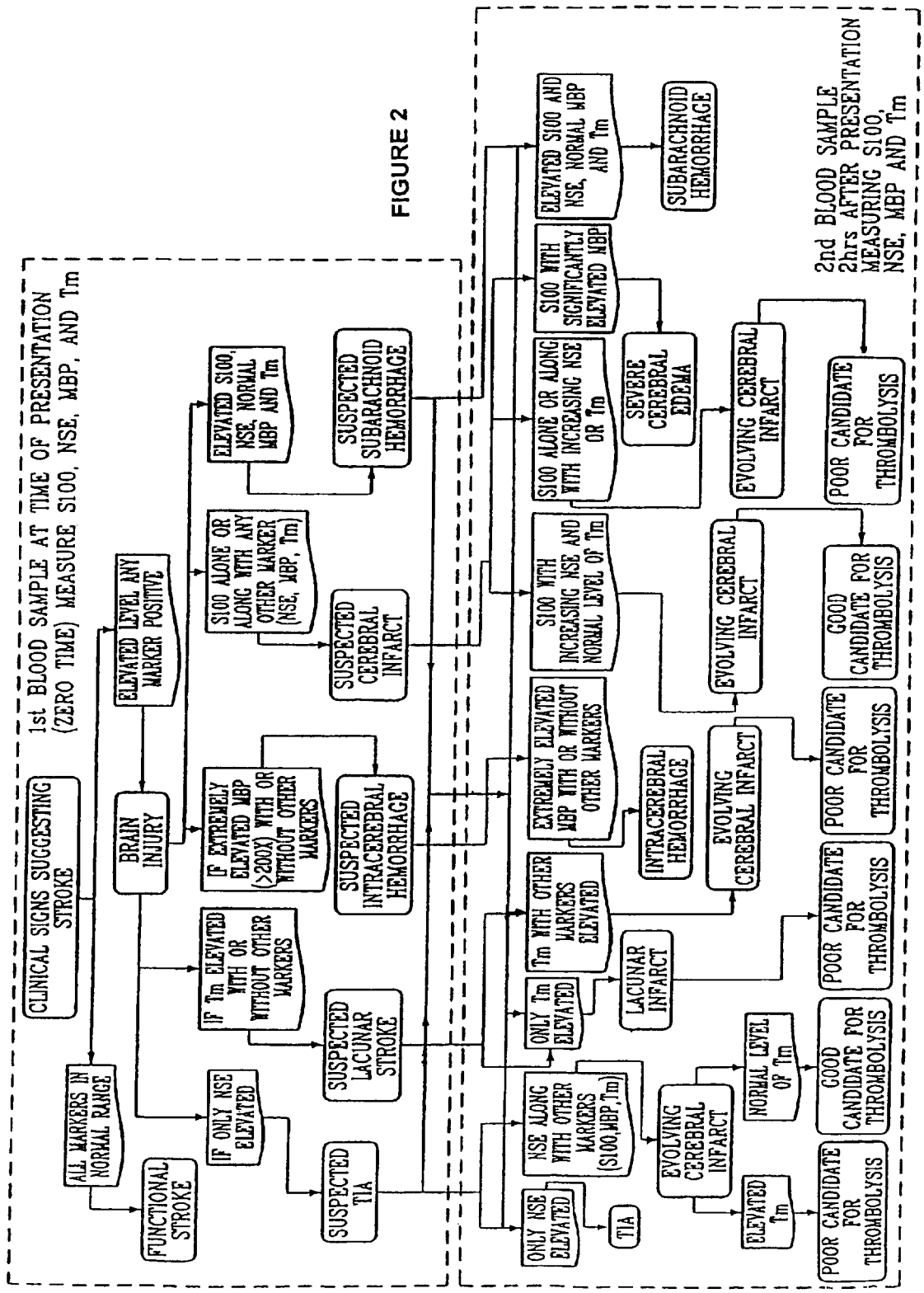
FIG. 2 is a flow chart illustrating how data obtained according to an embodiment of the invention can be used for the diagnosis of cerebral condition or status.

In a preferred embodiment of the invention body fluid samples taken from a patient at different points in time are analyzed. Typically a first body fluid sample is taken from a patient upon presentation with symptoms of stroke and analyzed according to the invention. Subsequently, some period of time after presentation, for example, about two hours after presentation, a second body fluid sample is taken and analyzed according to the invention. Referring now to FIG. 2 there is seen a flow chart illustrating how the data obtained from four marker proteins analyzed according to the invention, in the embodiment illustrated NSE, S100, MBP and Tm, can be used to triage the patient. The data can be used to diagnose stroke, rule out stroke, distinguish between thrombotic and hemorrhagic stroke, identify appropriate patients for thrombolytic treatment and determine how the stroke is evolving.

As stated previously, the level of each of the four specific markers in the patient's body fluid can be measured from one single sample or one or more individual markers can be measured in one sample and at least one marker measured in one or more additional samples. By "sample" is meant a volume of body fluid such as blood or CSF which is obtained at one point in time. Further, as will be discussed in detail below, all the markers can be measured with one assay device or by using a separate assay device for each marker in which case aliquots of the same fluid sample can be used or different fluid samples can be used. It is apparent that the analyses should be carried out within some short time frame after the sample is taken, e.g., within about one-half hour, so the data can be used to prescribe treatment as quickly as possible. It is preferred to measure each of the four markers in the same single sample, irrespective of whether the analyses are carried out in a single analytical device or in separate such devices so the level of each marker simultaneously present in a single sample can be used to provide meaningful data.

Generally speaking, the presence of each marker is determined using antibodies specific for each of the markers and detecting immunospecific binding of each antibody to its respective cognate marker. Any suitable immunoassay method may be utilized, including those which are commercially available, to determine the level of each of the specific markers measured according to the invention. Extensive discussion of the known immunoassay techniques is not required here since these are known to those of skill in the art. Typical suitable immunoassay techniques include sandwich enzyme-linked immunoassays (ELISA), radioimmunoassays (RIA), competitive binding assays, homogeneous assays, heterogeneous assays, etc. Various of the known immunoassay methods are reviewed in Methods in Enzymology, 70, pp. 30–70 and 166–198 (1980). Direct and indirect labels can be used in immunoassays. A direct label can be defined as an entity, which in its natural state, is visible either to the naked eye or with the aid of an optical filter and/or applied stimulation, e.g., ultraviolet light, to promote fluorescence. Examples of colored labels which can be used include metallic sol particles, gold sol particles, dye sol particles, dyed latex particles or dyes encapsulated in liposomes. Other direct labels include radionuclides and fluorescent or luminescent moieties. Indirect labels such as enzymes can also be used according to the invention. Various enzymes are known for use as labels such as, for example, alkaline phosphatase, horseradish peroxidase, lysozyme, glucose6-phosphate dehydrogenase, lactate dehydrogenase and urease. For a detailed discussion of enzymes in immunoassays see Engvall, Enzyme Immunoassay ELISA and EMIT, Methods of Enzymology, 70, 419–439 (1980).

A preferred immunoassay method for use according to the invention is a double antibody technique for measuring the level of the marker proteins in the patient's body fluid. According to this method one of the antibodies is a "capture" antibody and the other is a "detector" antibody. The capture antibody is immobilized on a solid support which may be any of various types which are known m the art such as, for example, microtiter plate wells, beads, tubes and porous materials such as nylon, glass fibers and other polymeric materials. In this method, a solid support, e.g., microtiter plate wells, coated with a capture antibody, preferably monoclonal, raised against the particular marker protein of interest, constitutes the solid phase. Diluted patient body fluid, e.g., serum or plasma, typically about 25 μl, standards and controls are added to separate solid supports and incubated. When the marker protein is present in the body fluid it is captured by the immobilized antibody which is specific for the protein. After incubation and washing, an anti-marker protein detector antibody, e.g., a polyclonal rabbit anti-marker protein antibody, is added to the solid support The detector antibody binds to marker protein bound to the capture antibody to form a sandwich structure. After incubation and washing an anti-IgG antibody, e.g., a polyclonal goat anti-rabbit IgG antibody, labeled with an enzyme such as horseradish peroxidase (HRP) is added to the solid support. After incubation and washing a substrate for the enzyme is added to the solid support followed by incubation and the addition of an acid solution to stop the enzymatic reaction.

The degree of enzymatic activity of immobilized enzyme is determined by measuring the optical density of the oxidized enzymatic product on the solid support at the appropriate wavelength, e.g., 450 nm for HRP. The absorbance at the wavelength is proportional to the amount of marker protein in the fluid sample. A set of marker protein standards is used to prepare a standard curve of absorbance vs marker protein concentration. This method is preferred since test results can be provided in 45 to 50 minutes and the method is both sensitive over the concentration range of interest for each marker and is highly specific.

The assay methods used to measure the marker proteins should exhibit sufficient sensitivity to be able to measure each protein over a concentration range from normal values found in healthy persons to elevated levels, i.e., 2SD above normal and beyond. Of course, a normal value range of the marker proteins can be found by analyzing the body fluid of healthy persons. For the S100b isoform where +2SD=0.02 ng/mL the upper limit of the assay range is preferably about 5.0 ng/mL. For NSE where +2SD=9.9 ng/mL the upper limit of the range is preferably about 60 ng/mL. For MBP, which has an elevated level cutoff value of 0.02 ng/mL, the upper limit of the assay range is preferably about 5.0 ng/mL and for Tm, which has an elevated level cutoff value of about 73 ng/mL, the assay range upper limit is preferably about 500 ng/mL.

The assays can be carried out in various assay device formats including those described in U.S. Pat. Nos. 4,906,439; 5,051,237 and 5,147,609 to PB Diagnostic Systems, Inc.

The assay devices used according to the invention can be arranged to provide a semiquantitative or a quantitative result By the term "semiquantitative" is meant the ability to discriminate between a level which is above the elevated marker protein value, and a level which is not above that threshold.

The assays may be carried out in various formats including, as discussed previously, a microtiter plate format which is preferred for carrying out the assays in a batch mode. The assays may also be carried out in automated immunoassay analyzers which are well known in the art and which can carry out assays on a number of different samples. These automated analyzers include continuous/random access types. Examples of such systems are described in U.S. Pat. Nos. 5,207,987 and 5,518,688 to PB Diagnostic Systems, Inc. Various automated analyzers that are commercially available include the OPUS® and OPUS MAGNUM® analyzers.

Another assay format which can be used according to the invention is a rapid manual test which can be administered at the point-of-care at any location. Typically, such point-of-care assay devices will provide a result which is above or below a threshold value, i.e., a semiquantitative result as described previously.

It should be recognized also that the assay devices used according to the invention can be provided to carry out one single assay for a particular marker protein or to carry out a plurality of assays, from a single volume of body fluid, for a corresponding number of different marker proteins. A preferred assay device of the latter type is one which can provide a semiquantitative result for the four primary marker proteins measured according to the invention, i.e., S100b, NSE, MBP and a brain endothelial marker protein, e.g., Tm. These device typically are adapted to provide a distinct visually detectable colored band at the location where the capture antibody for the particular marker protein is located when the concentration of the marker protein is above the threshold level. For a detailed discussion of assay types which can be utilized according to the invention as well as various assay formats and automated analyzer apparatus see U.S. Pat. No. 5,747,274 to Jackowski.

The invention will now be described further in detail with respect to specific preferred embodiments, it being understood that these are intended to be illustrative only and the invention is not limited to the materials, procedures, etc. recited therein.

EXAMPLE

A prospective observational pilot study was carried out at two tertiary care hospitals. The study evaluated thirty three patients admitted with a clinical and computed tomographic (CT) diagnosis of acute ischemic stroke. The mean age of the patients presenting with stroke was approximately 66 years (66.4±16.4) with an age range of from 27 to 90 years. The mean delay between the onset of symptoms and presentation to the hospital was 22 hours with a range of from 1 to 72 hours. Admission National Institutes of Health Stroke Scale and Discharge modified Rankin scale scores were recorded. Blood samples were obtained on days 1 (presentation), 3, 5 and 7 at one hospital and days 1, 2 and 3 at the second hospital. All blood samples were centrifuged and aliquots of serum were frozen and stored at −80° C. until analysis for S100, NSE, MBP and Tm.

Control subjects included one hundred three healthy blood donors (age range from 18 to 78 years; mean age 54.6±15.2 years) whose blood samples were used to determine reference values for concentrations of S100 and NSE and twenty four healthy blood donors who provided samples for reference measurements of MBP and Tm concentrations.

All reference values are reported as mean +2SD unless otherwise stated. The reference value for S100 in serum was 0.0067 ng/mL with a 98th percentile of 0.020 ng/mL. An elevated S100 value was taken as any concentration greater than the 98th percentile (0.02 ng/mL) of normal (normal +2SD=0.02 ng/mL).

The reference value for NSE in serum was 5.03±2.40 ng/mL. An elevated NSE value was any concentration greater than 2SD above normal, 9.85 ng/mL.

The reference value for MBP in serum was 0.0162±0.0019 ng/mL. An elevated MBP value was any concentration greater than 2SD above normal, 0.02 ng/mL.

The reference value for Tm in serum was 50.52±13.62 ng/mL. An elevated Tm value was any concentration greater than +2SD above normal, 76.14 ng/mL.

The levels of S100 and NSE were analyzed using Exact S100 and Exact NSE Elisa Assay Kits, respectively, available from Skye PharmaTech Inc., Mississauga, Canada The levels of Tm were analyzed with an ELISA assay available from Diagnostica Stago, 9 rue des Freres Chausson, 92600 Asneres Sur Seine, France. The level of MBP concentration was analyzed with an ELISA immunoassay from Diagnostic Systems Laboratories, Webster, Tex., United States.

In the tables showing the data obtained "D1" indicates the first day with the first blood sample being taken at the time of presentation. Subsequent days of sample collection are indicated by D2, D3, etc. For the values of the concentrations of the markers, +2SD are above the normal range. "ND" signifies that no data was obtained.

TABLE II

NSE, S100, MBP ND Tm CONCENTRATIONS IN CLINICAL SERUM SAMPLES

| CODE # | AGE | GENDER | NSE (ng/mL) + 2SD = 9.9 | S100 (ng/mL) + 2SD = 0.02 | MBP (ng/mL) + 2SD = 0.02 | Tm (ng/mL) + 2SD = 73 |
|---|---|---|---|---|---|---|
| SM-1 D1 | 42 | Female | 8.342 | 0.028 | 0.000 | 43.535 |
| SM-1 D3 | | | 13.300 | 1.098 | ND | 61.946 |
| SM-1 D5 | | | 9.622 | 0.060 | 0.238 | 65.859 |
| SM-1 D7 | | | 10.710 | 0.066 | 1.725 | 62.177 |
| DIAGNOSIS | | Left internal carotid. CEREBRAL INFARCT (arteroembolic). 5 h from onset of symptoms. | | | | |
| OUTCOME | | GOOD. Mild aphasia. | | | | |
| SM-2 D1 | 55 | Female | 9.420 | 0.053 | 0.032 | ND |
| SM-2 D3 | | | 5.430 | 0.015 | 0.105 | ND |
| SM-2 D5 | | | 7.360 | 0.011 | 0.341 | ND |
| SM-2 D7 | | | 9.906 | 0.008 | 0.124 | ND |
| DIAGNOSIS | | CEREBRAL INFARCT. Posterior circulation infarction (unknown mechanism). 20 h from onset of symptoms. | | | | |
| OUTCOME | | MODERATE. Dysarthia and hemiparesis. | | | | |
| SM-3 D1 | 78 | Male | 12.670 | 0.112 | 0.000 | 92.324 |
| SM-3 D3 | | | 14.980 | 0.719 | 1.420 | 101.990 |
| SM-3 D5 | | | 28.570 | 1.301 | 4.845 | 119.251 |
| DIAGNOSIS | | CEREBRAL INFARCT. Total anterior circulation infarction (cardioembolic). | | | | |
| OUTCOME | | DEATH | | | | |
| SM-4 D1 | 58 | Male | 8.520 | 0.008 | 0.000 | 73.913 |
| SM-4 D3 | | | 4.406 | 0.028 | 0.147 | 78.286 |
| SM-4 D5 | | | 4.888 | 0.024 | 0.265 | 85.881 |
| DIAGNOSIS | | CEREBRAL INFARCT. Lacunar circulation infarction (lacune). | | | | |
| OUTCOME | | GOOD. Mild ataxic hemiparesis. | | | | |
| SM-5 D2 | 27 | Male | 9.139 | 0.099 | 2.301 | 59.415 |
| SM-5 D3 | | | 5.492 | 0.000 | 0.090 | 53.892 |
| SM-5 D5 | | | 11.730 | 0.079 | 7.682 | 68.850 |
| SM-5 D7 | | | 11.540 | 0.018 | 10.382 | 68.620 |
| DIAGNOSIS | | CEREBRAL INFARCT (fibromuscular dysplasia). 48 h from onset of symptoms. | | | | |
| OUTCOME | | MODERATE. Aphasia and hemiparesis. | | | | |
| SM-6 D1 | 63 | Male | 7.029 | 0.000 | 0.000 | 56.883 |
| SM-6 D3 | | | 6.455 | 0.020 | 0.000 | 75.985 |
| DIAGNOSIS | | CEREBRAL INFARCT (unknown mechamism). 22 h from onset of symptoms. | | | | |
| OUTCOME | | MODERATE | | | | |
| SM-7 D1 | 64 | Female | 8.566 | 0.021 | 0.013 | 105.212 |
| SM-7 D3 | | | 5.061 | 0.024 | 0.000 | 129.146 |
| SM-7 D5 | | | 6.783 | 0.021 | 0.017 | 129.607 |
| SM-7 D8 | | | 7.377 | 0.015 | 0.000 | 162.746 |
| DIAGNOSIS | | CEREBRAL INFARCT. Lacunar circulation infarction (lacune). | | | | |
| OUTCOME | | MODERATE. Hemiparetic. | | | | |
| SM-8 D1 | 45 | Male | 15.740 | 0.053 | 0.009 | 37.092 |
| SM-8 D3 | | | 21.010 | 0.112 | 0.082 | 35.711 |
| DM-8 D5 | | | 15.060 | 0.095 | 0.112 | 38.703 |
| DIAGNOSIS | | CEREBRAL INFARCT (Right vertebral dissection). | | | | |
| OUTCOME | | GOOD. Minimal deficit. | | | | |
| SM-9 D1 | 35 | Male | 11.530 | 0.015 | 0.101 | ND |
| SM-9 D5 | | | 8.033 | 0.021 | 0.040 | ND |
| SM-9 D7 | | | 7.336 | 0.002 | 0.000 | ND |
| DIAGNOSIS | | CEREBRAL INFARCT (unknown mechanism). | | | | |
| OUTCOME | | GOOD. Minimal deficit. | | | | |

TABLE III

| CODE # | AGE | GENDER | NSE (ng/mL) + 2SD = 9.9 | S100 (ng/mL) + 2SD = 0.02 | MBP (ng/mL) + 2SD = 0.02 | Tm (ng/mL) + 2SD = 73 |
|---|---|---|---|---|---|---|
| SJ-01 D1 | 83 | MALE | 6.803 | 0.091 | 0.000 | 185.760 |
| SJ-01 D2 | | | 8.566 | 0.235 | 0.000 | 166.659 |
| SJ-01 D3 | | | 8.689 | 1.143 | 0.000 | 209.234 |
| DIAGNOSIS | | colspan | CEREBRAL INFARCT (recurrent). ↑BP, renal insufficiency, MI | | | |
| OUTCOME | | | Severe impairment developed on second day. | | | |
| SJ-02 D1 | 61 | MALE | 14.040 | 0.054 | 0.433 | 476.193 |
| SJ-02 D2 | | | 13.430 | 0.110 | 1.199 | 403.010 |
| SJ-02 D3 | | | 12.890 | 0.247 | 2.625 | 501.739 |
| DIAGNOSIS | | | CEREBRAL INFARCT (parietal infarction), renal failure, MI, CA. 48 h from onset of symptoms | | | |
| OUTCOME | | | First CT negative. Second CT positive (Day 3). DEATH (day 5) | | | |
| SJ-03 D1 | 83 | MALE | 10.700 | 0.000 | 0.000 | 75.064 |
| SJ-03 D2 | | | 8.926 | 0.000 | 0.000 | 81.968 |
| SJ-03 D3 | | | 9.000 | 0.000 | 0.000 | 89.793 |
| DIAGNOSIS | | | CEREBRAL INFARCT (lacune). ↑BP, DM | | | |
| OUTCOME | | | CT positive (Day 2) | | | |
| SJ-04 D1 | 70 | FEMALE | 10.270 | 0.000 | 0.000 | 134.209 |
| DIAGNOSIS | | | TIA. ↑BP, DM | | | |
| OUTCOME | | | | | | |
| SJ-05 D1 | 72 | MALE | 6.639 | 0.000 | 0.326 | 185.760 |
| SJ-05 D2 | | | 10.870 | 0.000 | 0.219 | 136.281 |
| SJ-05 D3 | | | 8.197 | 0.000 | 0.387 | 132.598 |
| DIAGNOSIS | | | CEREBRAL INFARCT (lacune), renal impairment | | | |
| OUTCOME | | | First CT negative | | | |
| SJ-06 D1 | 81 | FEMALE | 10.440 | 0.001 | 0.086 | ND |
| DIAGNOSIS | | | CEREBRAL INFARCT. Renal impairment (dialysis). 36 h from onset of symptoms | | | |
| OUTCOME | | | | | | |
| SJ-07 D1 | 90 | FEMALE | 12.540 | 0.001 | 0.162 | ND |
| DIAGNOSIS | | | CEREBRAL INFARCT. 36 h from onset of symptoms | | | |
| OUTCOME | | | | | | |
| SJ-08 D1 | 81 | MALE | 12.450 | 0.749 | 0.017 | 82.198 |
| DIAGNOSIS | | | HAEMORRHAGIC. 1 h from onset of symptoms | | | |
| OUTCOME | | | CT positive. DEATH 2 h later. | | | |
| SJ-09 D1 | 46 | MALE | 4.891 | 0.000 | 0.000 | 88.182 |
| SJ-09 D2 | | | 3.913 | 0.000 | 0.000 | 87.722 |
| SJ-09 D3 | | | 1.848 | 0.000 | 0.000 | 105.903 |
| DIAGNOSIS | | | STROKE (clinically). PA within 3 h of onset of symptoms | | | |
| OUTCOME | | | CT negative | | | |
| SJ-10 D1 | 69 | FEMALE | 8.303 | 0.000 | 0.000 | 79.437 |
| SJ-10 D2 | | | 6.000 | 0.000 | 0.000 | 74.144 |
| SJ-10 D3 | | | 3.939 | 0.000 | 0.000 | 68.850 |
| DIAGNOSIS | | | ~12 h from onset of symptoms<br>numbness in arms<br>R side facial droop; difficulty swallowing<br>no past Hx CVA<br>patient diabetic; has Hx high BP | | | |
| OUTCOME | | | Initial CT negative. All symptoms resolved; except patient still unable to swallow. | | | |
| SJ-11 D1 | 39 | MALE | 10.770 | 0.058 | 0.063 | 65.398 |
| SJ-11 D2 | | | 12.050 | 0.047 | 0.128 | 69.311 |
| SJ-11 D3 | | | 17.330 | 0.068 | 0.189 | 76.675 |
| DIAGNOSIS | | | CEREBRAL INFARCT. ~24 h from onset of symptoms<br>found unconscious with R-sided neglect | | | |
| OUTCOME | | | CT positive (Day 1)<br>3 lesions present ~2 cm<br>basal ganglia L side<br>Patient still has severe weakness R side with speech impairment | | | |
| SJ-12 D1 | 51 | FEMALE | 11.700 | 0.000 | 0.067 | 286.100 |
| SJ-12 D2 | | | 8.788 | 0.000 | 0.055 | 270.911 |
| SJ-12 D3 | | | 11.800 | 0.002 | 0.124 | 226.264 |
| DIAGNOSIS | | | CEREBRAL INFARCT (lacune).<br>~12 h from onset of symptoms<br>weakness L side, esp. L arm<br>facial droop and pronounced slurring of speech<br>Bell's Palsy L side<br>renal dialysis patient | | | |

TABLE III-continued

| CODE # | AGE | GENDER | NSE (ng/mL) + 2SD = 9.9 | S100 (ng/mL) + 2SD = 0.02 | MBP (ng/mL) + 2SD = 0.02 | Tm (ng/mL) + 2SD = 73 |
|---|---|---|---|---|---|---|
| OUTCOME | | CT positive (Day 1 developed thrombocytopenia Day 2 | | | | |
| SJ-13 D1 | 78 | FEMALE | 10.090 | 0.000 | 0.000 | 46.297 |
| SJ-13 D2 (Haemolytic) | | | 40.040 | 0.768 | 0.433 | 41.924 |
| SJ-13 D3 | | | 4.667 | 0.103 | 0.000 | 36.861 |
| DIAGNOSIS | | CEREBRAL INFARCT (Left MCA CVA) + CAD, + Diabetic, Hx HTN, + family Hx CVA. ~19 h from onset of symptoms | | | | |
| OUTCOME | | Initial CT negative. Initial Symptoms worsened over 48 h to R hemiplegia. | | | | |
| SJ-14 D1 | 72 | MALE | 7.303 | 0.087 | 0.299 | NC |
| SJ-14 D2 | | | 5.697 | 0.007 | 0.055 | NC |
| DIAGNOSIS | | CEREBRAL INFARCT (Left CVA). ~9 h from onset of symptoms prior CVA 1989 Hx strial fib., anticoagulated MI 1997 | | | | |
| OUTCOME | | Symptoms improving | | | | |
| SJ-15 D1 | 79 | MALE | 5.667 | 0.000 | 0.013 | ND |
| DIAGNOSIS | | CEREBRAL INFARCT (Left CVA) symptoms progressive over 2 wk period; worsened over 3 day period just prior to presentation at hospital. | | | | |
| OUTCOME | | CT negative Day 1 condition worsening at discharge (discharged at family's request for palliative care at home) | | | | |
| SJ-16 D1 | 90 | FEMALE | 20.940 | 0.811 | 5.142 | 52.281 |
| SJ-16 D2 | | | 12.220 | 0.498 | 5.459 | 55.733 |
| SJ-16 D3 | | | 9.424 | 0.253 | 3.377 | 55.503 |
| DIAGNOSIS | | Large intracerebral bleed with smaller subdural hematoma and intraventricular hemorrhage Onset of symptoms unknown (6 to 29 h prior) previously well; no Hx other than colon Ca 20 yr prior; on no meds at home; found collapsed | | | | |
| OUTCOME | | Patient continues to worsen | | | | |
| SJ-17 D1 | 77 | MALE | 10.660 | 0.042 | 0.002 | ND |
| SJ-17 D2 | | | 8.758 | 0.095 | 0.006 | ND |
| SJ-17 D3 | | | 12.510 | 0.261 | 0.417 | ND |
| DIAGNOSIS | | CEREBRAL INFARCT (Right CVA) old left cerebellar infarct sudden onset; slurred speech and L-sided weakness ~15 h from onset of symptoms | | | | |
| OUTCOME | | CT showed old CVA and new right MCA infarct | | | | |
| SJ-18 D1 | 79 | MALE | 21.560 | 0.008 | 0.000 | 61.946 |
| SJ-18 D2 | | | 14.390 | 0.218 | 0.814 | 48.598 |
| SJ-18 D3 | | | 11.050 | 0.102 | 0.698 | 55.963 |
| DIAGNOSIS | | Initial CT showed bleed or cerebral edema. ~2 h from onset of symptoms | | | | |
| OUTCOME | | Aphasia and R-sided weakness | | | | |
| SJ-19 D1 | 82 | FEMALE | 9.948 | 0.000 | ND | 64.248 |
| SJ-19 D2 | | | 9.781 | 0.008 | ND | 58.955 |
| SJ-19 D3 | | | 11.720 | 0.023 | ND | 64.248 |
| DIAGNOSIS | | TIA ~24 h from onset of symptoms | | | | |
| OUTCOME | | Slurred speech, difficulty swallowing which persists. | | | | |
| SJ-20 D1 | ND | MALE | 26.400 | 0.122 | 0.000 | 32.719 |
| DIAGNOSIS | | Haemorrhagic stroke | | | | |
| OUTCOME | | | | | | |
| SJ-21 D1 | 74 | MALE | 5.828 | 0.016 | ND | 74.374 |
| SJ-21 D2 | | | 7.423 | 0.063 | ND | 75.985 |
| SJ-21 D3 | | | 8.436 | 0.286 | ND | 71.382 |
| DIAGNOSIS | | CEREBRAL INFARCT (left CVA) | | | | |
| OUTCOME | | R-sided weakness | | | | |
| SJ-22 D1 (Haemolytic) | 63 | FEMALE | 18.600 | 0.000 | 0.000 | ND |
| SJ-22 D2 | | | 9.540 | 0.008 | 0.000 | ND |
| DIAGNOSIS | | CEREBRAL INFARCT (left CVA), initial CT negative | | | | |
| OUTCOME | | weakness (resolving) | | | | |
| SJ-23 D1 | 79 | MALE | 14.530 | 2.009 | 5.478 | ND |
| SJ-23 D2 | | | 23.980 | >3.200 | 8.155 | ND |
| SJ-23 D3 | | | 27.670 | 2.218 | 7.309 | ND |

TABLE III-continued

| CODE # | AGE | GENDER | NSE (ng/mL) + 2SD = 9.9 | S100 (ng/mL) + 2SD = 0.02 | MBP (ng/mL) + 2SD = 0.02 | Tm (ng/mL) + 2SD = 73 |
|---|---|---|---|---|---|---|
| DIAGNOSIS | | CEREBRAL INFARCT, CT positve | | | | |
| OUTCOME | | CT showed multiple cerebral infarcts. | | | | |
| SJ-24 D1 | 73 | MALE | 20.630 | 0.000 | 0.000 | 74.160 |
| SJ-24 D2 | | | 17.880 | 0.000 | 0.000 | 89.750 |
| SJ-24 D3 | | | 17.880 | 0.000 | 0.000 | 83.290 |
| DIAGNOSIS | | TIA | | | | |
| | | sudden decrease in ability to function, word difficulties | | | | |
| OUTCOME | | CT negative | | | | |
| | | Discharged with diagnosis of TIA | | | | |

The analysis of S100, NSE and MBP levels in serum samples from healthy control subjects showed no relationship of levels of these proteins to age or sex. In the case of Tm, the concentrations were higher in serum samples from healthy males than in females (54.62±13.62 ng/mL, 2SD above normal=81.86 ng/mL and 43.63±11.18 ng/mL, 2SD above normal=68.74 ng/mL, respectively).

Of the thirty three stroke patients twenty six were infarcts (79%) and of these five were lacunar (15%) and four had hemorrhagic stroke (12%). Of the hemorrhagic stroke patients three had subarachnoid hemorrhage and one had an intracerebral bleed. Three patients (9%) had transient ischemic attacks (TIA).

On presentation the levels of S100 were elevated in 44% of the patients, NSE levels were elevated in 59%, MBP levels were elevated in 40% and Tm levels were elevated in 57%.

The data indicate that by measuring the four marker proteins in accordance with the invention, where any one marker was elevated, 94% of the patients could be identified on presentation. Nineteen of the twenty one non-lacunar infarcts (90%) could be identified on presentation. The remaining two patients arrived at the hospital at 22 and 72 hours respectively after onset of symptoms.

Each of FIGS. 3–10 is a graphical illustration of the data obtained from a different patient of the study. The concentration levels are expressed as multiples of a reference value and were obtained by dividing the actual measured concentration values by the defined reference value for each respective marker protein, i.e., the 2SD value.

Figure 3:
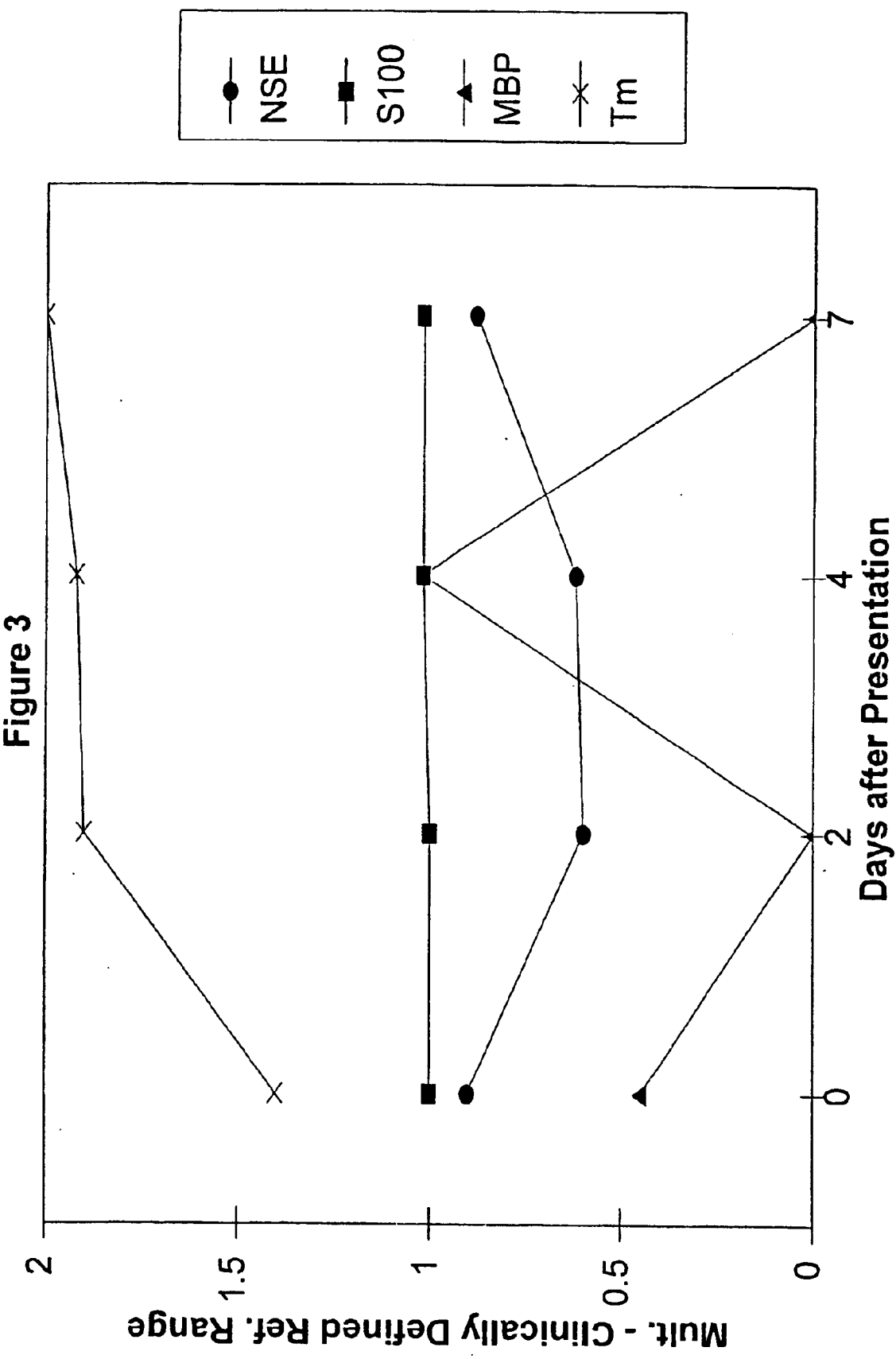
FIG. 3 illustrates that, for patient SM7, the only elevated marker protein was Tm indicating a lacunar infarct.

All lacunar infarcts, hemorrhagic and TIA patients were identified on presentation with 100% accuracy. All five lacunar infarcts had elevated levels of Tm on presentation. In some patients the only elevated marker protein was Tm. Referring now to FIG. 3 it can be seen that, for patient SM7, the only elevated marker protein was Tm indicating a lacunar infarct.

Figure 4:
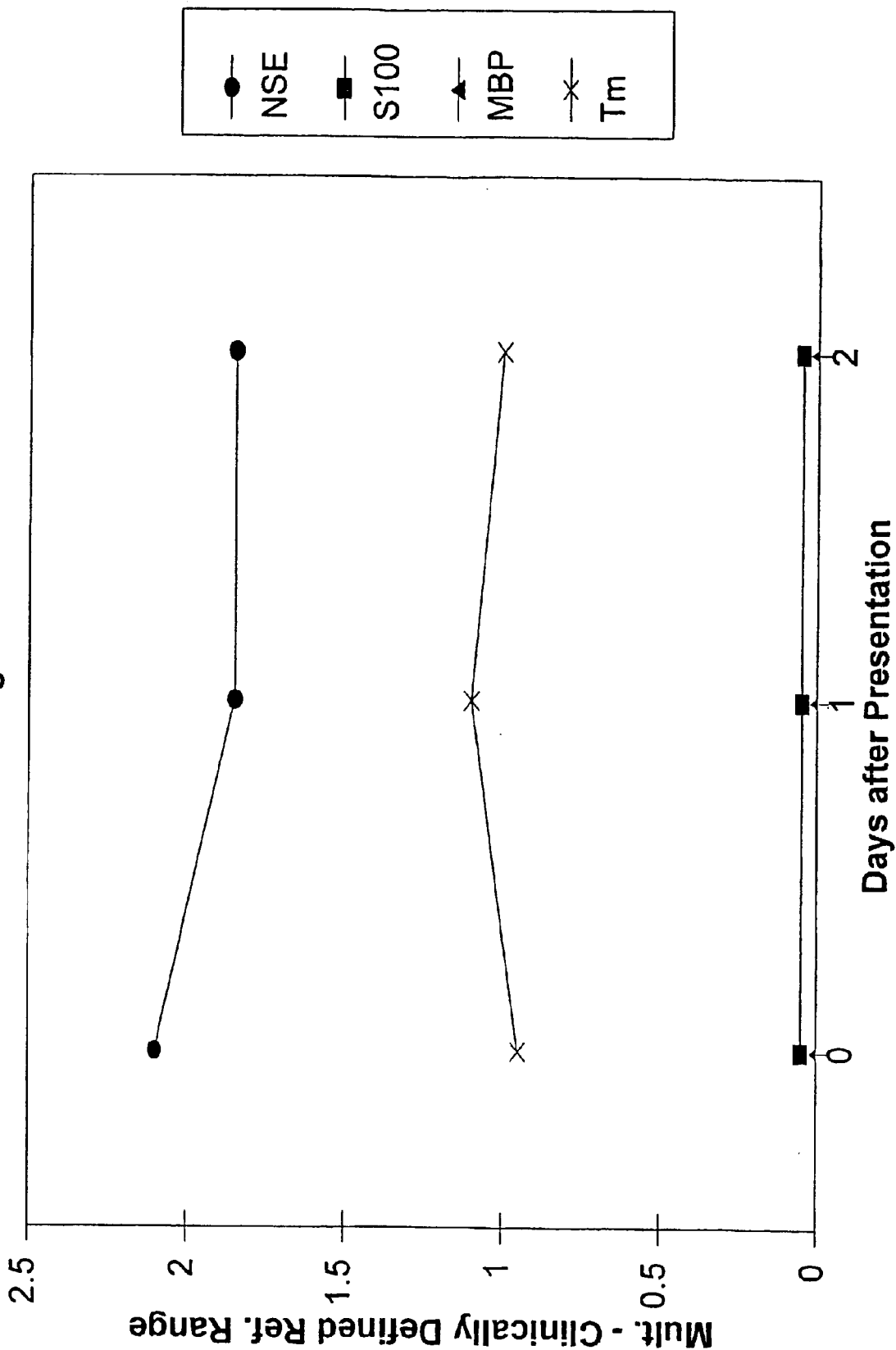
FIG. 4 illustrates that for patient SM-24, Tm was slightly elevated and NSE was elevated indicating a TIA.
Figure 5:
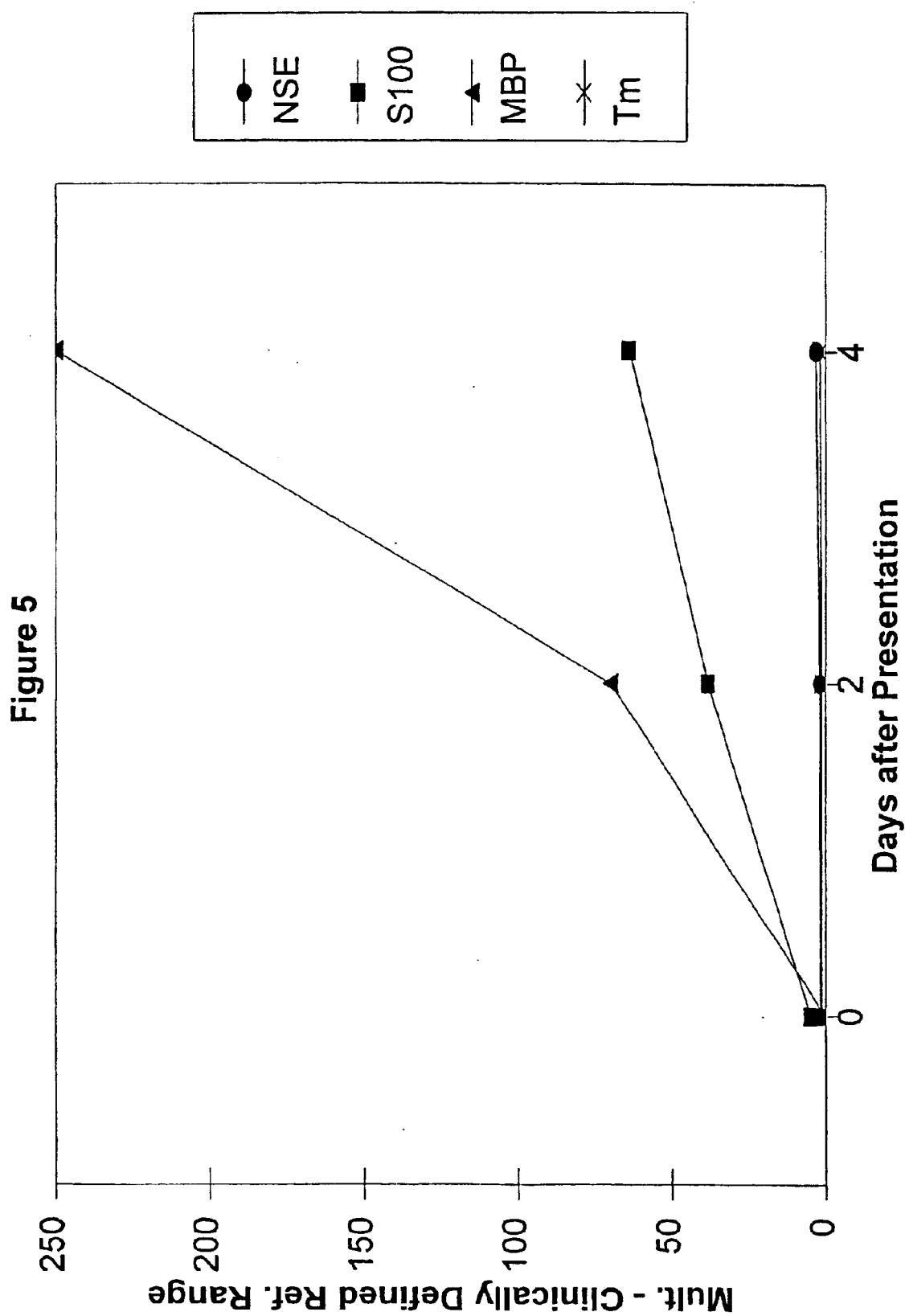
FIG. 5 illustrates that patient SM-3 had greatly elevated levels of MBP and S100 as well as elevated levels of NSE and Tm indicating a cerebral infarct with damage spreading into the base of the brain.

The three TIA patients had elevated NSE levels and normal S100 and MBP levels that stayed within the normal range. Tm was elevated in one of the TIA patients. Referring now to FIG. 4 it can be seen that for patient SM-24, Tm was slightly elevated and NSE was elevated indicating a TIA. The patient was discharged with diagnosis of TIA. Referring now to FIG. 5 it can be seen that patient SM-3 had greatly elevated levels of MBP and S100 as well as elevated levels of NSE and Tm indicating a cerebral infarct with damage spreading into the base of the brain.

Figure 6:
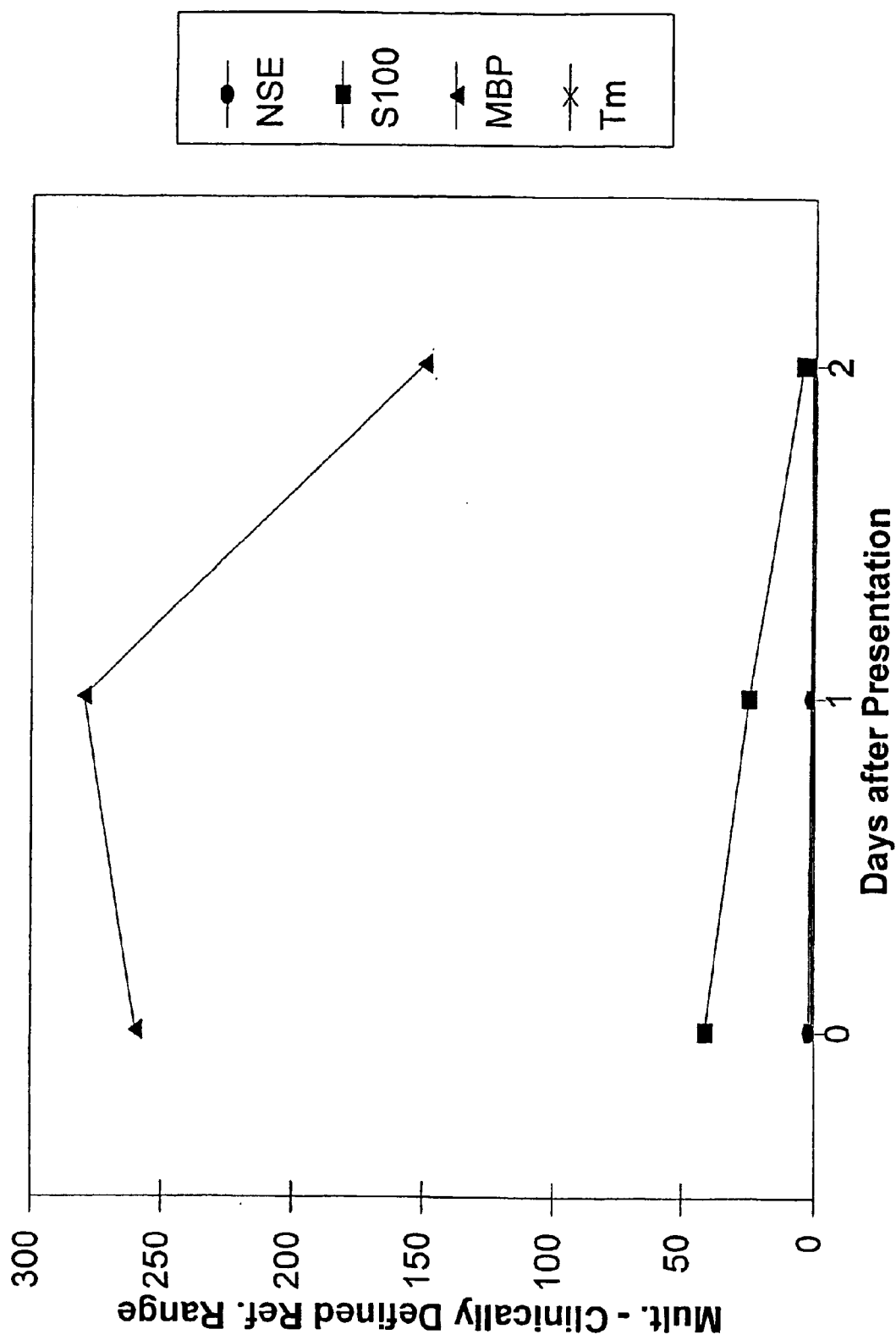
FIG. 6 illustrates that patient SJ-16 had a 250 fold increased level of MBP upon presentation as well as elevated levels of S100 and NSE and had suffered an intracerebral hemorrhage.

In the four hemorrhagic stroke patients, the three subarachnoid hemorrhagic patients had elevated levels of S100 and NSE and a normal Tm level. In the patient with an intracerebral hemorrhagic stroke the levels of S100 and NSE were elevated and the level of MBP was elevated about 250 times. FIG. 6 illustrates that patient SJ-16 had a 250 fold increased level of MBP upon presentation as well as elevated levels of S100 and NSE and had suffered an intracerebral hemorrhage.

Figure 7:
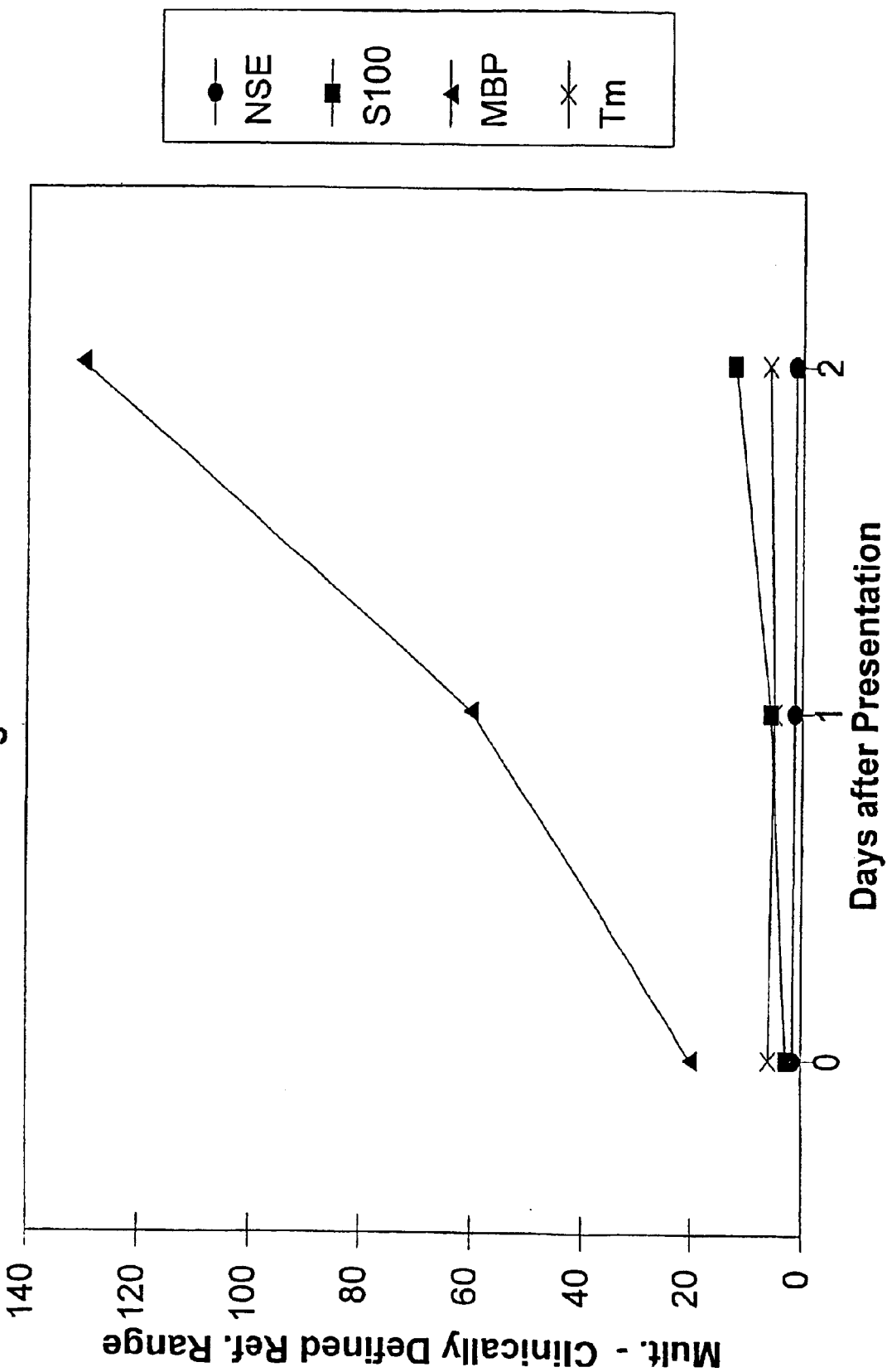
FIG. 7 illustrates that patient SJ-2 had elevated MBP, Tm and S100 upon presentation and that the MBP and S100 levels continued to increase with time indicating a cerebral infarct with the stroke increasing over time.

FIG. 7 illustrates that patient SJ-2 had elevated MBP, Tm and S100 upon presentation and that the MBP and S100 levels continued to increase with time indicating a cerebral infarct with the stroke increasing over time. An initial CAT scan upon presentation was negative and became positive only days later.

Figure 8:
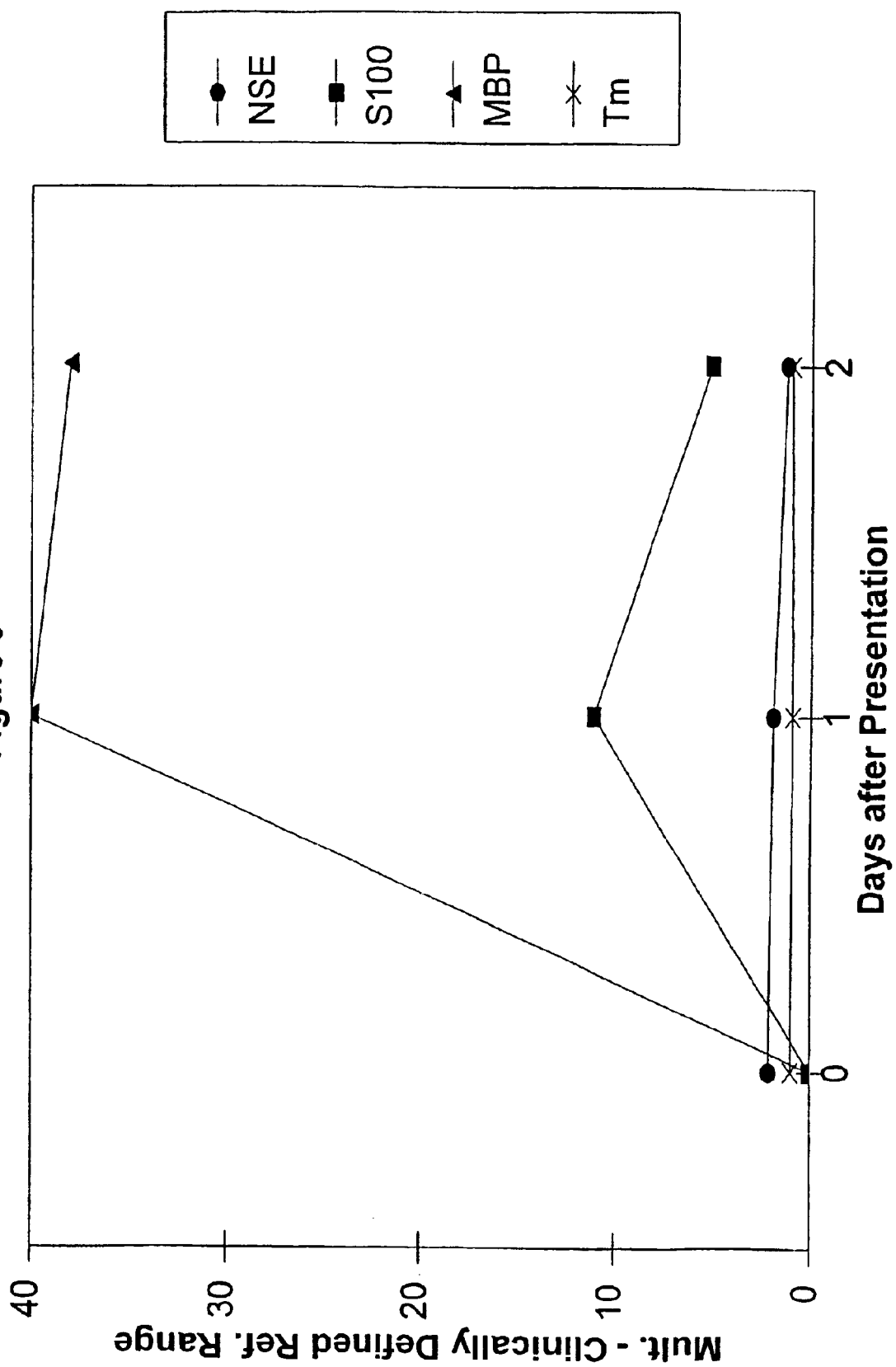
FIG. 8 illustrates that patient SJ-18 presented with a TIA which evolved into a stroke. Tm was in the normal range indicating that the cerebral vasculature was not compromised and thus indicating that the patient was a good candidate for thrombolysis.

FIG. 8 illustrates that patient SJ-18 presented with a TIA which evolved into a stroke. Tm was in the normal range indicating that the cerebral vasculature was not compromised and thus indicating that the patient was a good candidate for thrombolysis.

Figure 9:
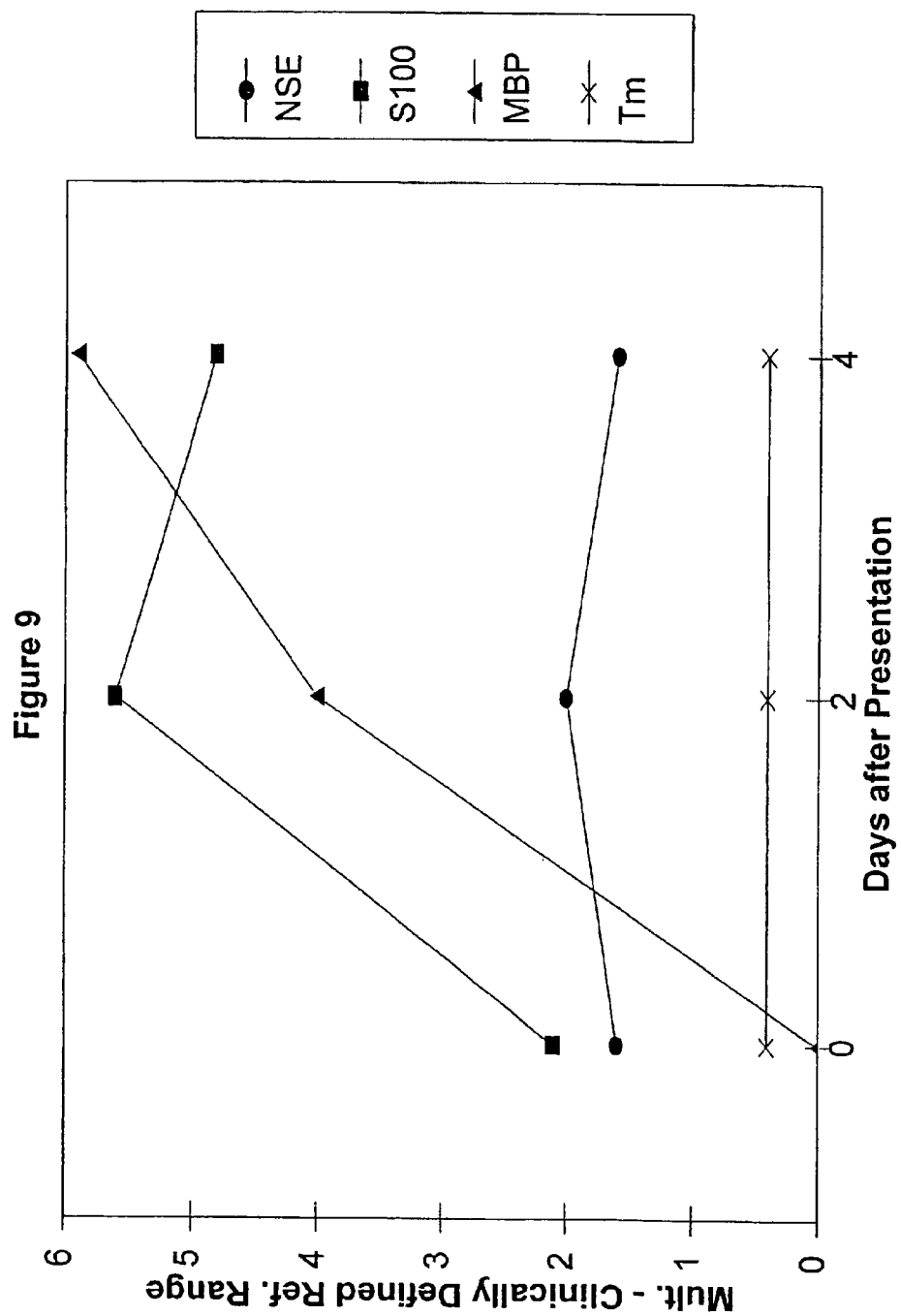
FIG. 9 illustrates that patient SM-8 presented with a cerebral infarct and, with Tm in the normal range, was a good candidate for thrombolysis since the endothelial vasculature was not compromised.

FIG. 9 illustrates that patient SM-8 presented with a cerebral infarct and, with Tm in the normal range, was a good candidate for thrombolysis since the endothelial vasculature was not compromised.

FIG. 10 illustrates that patient SJ-1 had a cerebral infarct and because of the elevated Tm level was at risk of hemorrhage if given thrombolytics because of the endothelial vasculature being compromised.

For the second serum sample obtained the levels of S100 were elevated in 73% of the stroke patients, the NSE levels in 54%, MBP levels in 64% and Tm levels in 55%. These data indicated that by measuring the four marker proteins in accordance with the invention, where any one marker was elevated 96% of the patients could be identified from the second serum sample obtained.

The data indicate that the levels of the protein markers in subsequent serum samples either increased or decreased depending upon whether the stroke was evolving in severity or subsiding.

Eighteen (54%) of the thirty three stroke patients had a CAT scan performed on presentation. All four hemorrhagic stroke patients were CAT positive at presentation. Nine (50%) of the eighteen patients had a normal CAT at presentation which became positive days later. Eight of these nine patients who had a normal CAT on presentation had elevated levels of one or more of the four protein markers on presentation. All of the nine CAT positive patients on presentation also had elevated levels of one or more protein markers on presentation.

Peak S100, NSE and MBP levels were significantly correlated (Pearson's) with admission N1HSS scores ($p<0.05$) and discharge modified Rankin scores ($p<0.05$).

The data show that levels of S100, NSE, MBP and Tm can be easily and reliably measured in acute ischemic stroke patients and that by measuring these four marker proteins in accordance with the invention, when any one marker protein is elevated a 94% sensitivity for acute ischemic stroke can be achieved upon presentation. Further, in the hyperacute period of the evolving stroke, elevated levels of one or more of these four marker proteins appear to precede irreversible tissue damage and brain edema prior to detection of such damage by CAT.

Although the invention has been described with respect to various preferred embodiments it is not intended to be limited thereto but rather those skilled in the art will recognize that variations and modifications may be made therein which are within the spirit of the invention and the scope of the appended claims.

What is claimed is:

1. A method for determining the occurrence of a cerebral event and differentially diagnosing between an ischemic cerebral event and a hemorrhagic cerebral event comprising:
   a. analyzing a body fluid of a patient to detect presence and concentration level of ischemic marker proteins, said ischemic marker proteins consisting of myelin basic protein (MBP), the beta isoform of S 100 protein (S 100), and neuronal specific enolase (NSE), said analyzing comprising contacting said MBP, the beta isoform of S100 and NSE with a reagent capable of detecting said marker proteins, detecting each of said marker proteins, and removing reagent that does not detect said marker proteins,
   b. analyzing a body fluid of said patient to detect presence and concentration level of a brain endothelial cell membrane protein, said analyzing comprising contacting said brain endothelial cell membrane protein with a reagent capable of detecting said endothelial cell membrane protein, detecting said endothelial cell membrane protein, and removing reagent that does not detect said brain endothelial cell membrane protein,
   c. comparing the concentration level of each protein detected in steps (a) and (b) to specific threshold values to determine the presence of statistically significant concentrations thereof,
   d. assessing patient condition by comparing said presence or absence of statistically significant concentrations of said protein in accordance with an analytical flowchart; and
   e. determining whether the patient condition assessed in step (d) is an ischemic cerebral event or an hemorrhagic cerebral event, wherein if only said NSE is elevated, or if only said brain endothelial cell membrane protein is elevated, or if S100 is present alone or along with any of NSE, MBP or a brain endothelial cell membrane, then said patient condition is indicative of an ischemic cerebral event; unless MBP is present at a level 200 times normal or greater, or unless S100 and NSE levels are elevated, and MBP and brain endothelial membrane protein levels are normal, then said patient condition is indicative of a hemorrhagic cerebral event.

2. A method as defined in claim 1, wherein said body fluid is selected from the group consisting of blood, a blood product and cerebrospinal fluid.

3. A method as defined in claim 1, wherein said brain endothelial cell membrane protein is selected from one or more of the group consisting of Thrombomodulin, Glucose Transporter I in the dimeric or tetrameric form, Neurothelin, Gamma Glutamyl Transpeptidase, and P-glycoprotein.

4. A method as defined in claim 3 wherein said brain endothelial cell membrane protein is Thrombomodulin.

5. A method as defined in claim 1 further comprising:
   analyzing said body fluid to detect presence and concentration level of a secondary marker protein, said secondary marker protein being from the cell type of one of said myelin basic protein, beta isoform of S100 protein or neuronal specific enolase, whereby the time of onset of a hemorrhagic or ischemic cerebral event can be determined.

6. A method as defined in claim 5 wherein said secondary marker protein has a higher molecular weight than said corresponding myelin basic protein, beta isoform of S100 protein or neuronal specific enolase.

7. A method as defined in claim 1 wherein each of said analyses is carried out on a single sample of body fluid.

8. A method as defined in claim 1 wherein at least one of said analyses is carried out on a first sample of body fluid and at least another of said analyses is carried out on a second sample of body fluid.

9. A method as defined in claim 8 wherein said first and said second samples of body fluid are taken at different time periods.

10. A method as defined in claim 1 wherein a plurality of samples of said body fluid are obtained at predefined time intervals and analyzed and the information from said analyses compared as a function of time whereby the progression of an ischemic or hemorrhagic cerebral event can be determined.

11. A method as defined in claim 1 wherein each of said analyses comprises contacting said body fluid with an antibody which is specific for said protein.

12. A method as defined in claim 11 wherein at least one of said analyses is carried out with an enzyme-labeled immunoassay method.

13. A method for diagnosing an ischemic or hemorrhagic cerebral event comprising:
   (a) analyzing a body fluid of a patient to detect the presence and concentration level of four proteins comprising myelin basic protein (MBP), the beta isoform of S100 protein (S100), neuronal specific enolase (NSE) and a brain endothelial cell membrane protein;
   (b) comparing the concentration level of each said protein detected in step (a) to specific threshold values to determine the presence of a statistically significant concentration thereof;
   (c) assessing patient condition by comparing said presence or absence of statistically significant concentrations of said proteins in accordance with an analytical flow chart; and
   (d) determining whether the patient condition assessed in step (c) is an ischemic cerebral event or an hemorrhagic cerebral event, wherein if only said NSE is elevated, or if only said brain endothelial cell membrane protein is elevated, or if S100 is present alone or along with any of NSE, MBP or a brain endothelial cell membrane, then said patient condition is indicative of an ischemic cerebral event; unless MBP is present at a level 200 times normal or greater, or unless S100 and NSE levels are elevated, and MBP and brain endothelial membrane protein levels are normal, then said patient condition is indicative of a hemorrhagic cerebral event.

14. The method of claim 13 wherein said protein(s) are present at a statistically significant concentration if the concentration of said protein is about two standard deviations above normal levels.

15. The method of claim 13 wherein said brain endothelial cell membrane protein is selected from the group consisting of thrombomodulin, glucose transporter I (dimeric form), glucose transporter I (tetrameric form), neurothelin, gamma glutamyl transpeptidase, and p-glycoprotein.

16. The method of claim 1 or 13 wherein at least one of said analyses in step (a) is conducted on a first sample of body fluid and at least another of said analyses in step (a) is carried out on a second sample of body fluid.

17. The method of claim 16, wherein said first sample and said second sample of body fluid are taken at different times.

18. The method of claim 13 further comprising assessing the type of ischemic or hemorrhagic cerebral event, wherein the presence of only NSE at a statistically significant concentration is indicative that said cerebral event is a transitory ischemic attack (TIA).

19. The method of claim 13 further comprising assessing the type of ischemic or hemorrhagic cerebral event, wherein the presence of NSE and one or more proteins selected from the group consisting of MBP, S100, and a brain endothelial cell membrane protein at a statistically significant concentration is indicative that said cerebral event is a cerebral infarction.

20. The method of claim 13 further comprising assessing the type of ischemic or hemorrhagic cerebral event, wherein the presence of only a brain endothelial cell membrane protein at a statistically significant concentration is indicative that said cerebral event is a lunar infarction.

21. The method of claim 13 further comprising assessing the type of ischemic or hemorrhagic cerebral event, wherein the presence of a brain endothelial cell membrane protein and one or more proteins selected from the group consisting of MBP, S100, and NSE at statistically significant concentrations is indicative that said cerebral event is a cerebral infarction.

22. The method of claim 13 further comprising assessing the type of ischemic or hemorrhagic cerebral event, wherein the presence of MBP at a concentration of greater than about 200 times the normal level is indicative that said cerebral event is an intracerebral hemorrhage.

23. The method of claim 13 further comprising assessing the type of ischemic or hemorrhagic cerebral event, wherein the presence of S100 at a statistically significant concentration is indicative that said cerebral event is a cerebral infarction or a subarachnoid hemorrhage.

24. The method of claim 13 further comprising assessing the type of ischemic or hemorrhagic cerebral event, wherein the presence of S100 and NSE at a statistically significant concentration and the absence of any other markers is indicative that said cerebral event is a subarachnoid hemorrhage.

25. The method of claim 1, wherein if only NSE is present, then said ischemic cerebral event is a transitory ischemic attack.

26. The method of claim 1, wherein if only a brain endothelial cell membrane protein is present, then said ischemic cerebral event is a lacunar infarct.

27. The method of claim 1, wherein if S100 is present or if NSE along with any of MBP, S100 or a brain endothelial cell membrane protein are present, or if brain endothelial cell membrane protein, with any one of MBP, NSE, or S100, or if S100 is present with elevated NSE and normal levels of a brain endothelial cell membrane protein, then said ischemic cerebral event is an evolving cerebral infarct.

28. The method of claim 1, wherein if MBP is present at a level about 200 times normal or greater, then said hemorrhagic cerebral event is an intracerebral edema.

29. The method of claim 1, wherein if S100 and NSE are elevated, and MBP and brain endothelial cell membrane protein levels are normal, then said hemorrhagic cerebral event is a subarachnoid hemorrhage.

30. The method of claim 1, wherein if S100 and MBP are elevated, then said hemorrhagic cerebral event is a cerebral edema.

* * * * *